US011395669B2

(12) United States Patent
O'Malley et al.

(10) Patent No.: US 11,395,669 B2
(45) Date of Patent: Jul. 26, 2022

(54) CLOT RETRIEVAL DEVICE WITH FLEXIBLE COLLAPSIBLE FRAME

(71) Applicant: Neuravi Limited, Galway (IE)

(72) Inventors: Thomas O'Malley, Galway (IE); Aidan Duffy, Galway (IE); Declan Lee, Galway (IE); AnnaLisa Smullin, Galway (IE); Gillian Gunning, Galway (IE); Diarmaid O'Keeffe, Galway (IE)

(73) Assignee: Neuravi Limited, Galway (IE)

( * ) Notice: Subject to any disclaimer, the term of this patent is extended or adjusted under 35 U.S.C. 154(b) by 0 days.

(21) Appl. No.: 16/946,464

(22) Filed: Jun. 23, 2020

(65) Prior Publication Data
US 2021/0393278 A1    Dec. 23, 2021

(51) Int. Cl.
*A61B 17/221*     (2006.01)
*A61B 90/00*      (2016.01)

(52) U.S. Cl.
CPC ............ *A61B 17/221* (2013.01); *A61B 90/39* (2016.02); *A61B 2017/2212* (2013.01); *A61B 2090/3966* (2016.02)

(58) Field of Classification Search
CPC .......... A61B 17/221; A61B 2017/2215; A61B 2017/2212; A61B 2017/22035; A61B 2017/22034; A61B 17/320725; A61B 2017/320716; A61F 2/012; A61F 2/013; A61F 2/014; A61F 2/015; A61F 2002/9528; A61F 2002/9534
See application file for complete search history.

(56) References Cited

U.S. PATENT DOCUMENTS

| | | | |
|---|---|---|---|
| 2,828,147 A | 3/1958 | Peiffer | |
| 3,361,460 A | 1/1968 | Gerhart | |
| 4,455,717 A | 6/1984 | Gray | |
| 4,611,594 A | 9/1986 | Grayhack et al. | |
| 4,612,931 A | 9/1986 | Dormia | |

(Continued)

FOREIGN PATENT DOCUMENTS

| | | |
|---|---|---|
| CN | 2557083 Y | 6/2003 |
| CN | 101172051 A | 5/2008 |

(Continued)

OTHER PUBLICATIONS

US 6,348,062 B1, 02/2002, Hopkins (withdrawn)
(Continued)

*Primary Examiner* — Wade Miles
(74) *Attorney, Agent, or Firm* — Troutman Pepper Hamilton Sanders LLP

(57) ABSTRACT

A clot retrieval device includes an inner expandable member and an outer expandable member, each formed from respective strut frameworks such that the outer expandable member has larger cell openings than the inner expandable member. The outer expandable member can have multiple discontinuous body segments spaced apart in relation to a longitudinal axis of the device. Adjacent discontinuous body segments can be joined by a pair of tapered connecting arms that are able to bend with a small radius of curvature compared to the body segments. Some or all of the body segments can include radiopaque markers positioned to illustrate a circumference of the respective body segment and slightly staggered in relation to a longitudinal axis of the device such that the markers nest when the device is collapsed for delivery.

19 Claims, 14 Drawing Sheets

(56) References Cited

U.S. PATENT DOCUMENTS

| | | |
|---|---|---|
| 4,793,348 A | 12/1988 | Palmaz |
| 4,873,978 A | 10/1989 | Ginsburg |
| 5,011,488 A | 4/1991 | Ginsburg |
| 5,084,065 A | 1/1992 | Weldon et al. |
| 5,092,839 A | 3/1992 | Kipperman |
| 5,100,423 A | 3/1992 | Fearnot |
| 5,102,415 A | 4/1992 | Guenther et al. |
| 5,108,419 A | 4/1992 | Reger et al. |
| 5,122,136 A | 6/1992 | Guglielmi et al. |
| 5,163,951 A | 11/1992 | Pinchuk et al. |
| 5,171,233 A | 12/1992 | Amplatz |
| 5,171,259 A | 12/1992 | Inoue |
| 5,217,441 A | 6/1993 | Shichman |
| 5,234,437 A | 8/1993 | Sepetka |
| 5,236,447 A | 8/1993 | Kubo et al. |
| 5,330,482 A | 7/1994 | Gibbs |
| 5,383,887 A | 1/1995 | Nadal |
| 5,387,219 A | 2/1995 | Rappe |
| 5,387,226 A | 2/1995 | Miraki |
| 5,449,372 A | 9/1995 | Schmaltz |
| 5,499,985 A | 3/1996 | Hein et al. |
| 5,538,512 A | 7/1996 | Zenzon et al. |
| 5,538,515 A | 7/1996 | Kafry et al. |
| 5,549,626 A | 8/1996 | Miller et al. |
| 5,558,652 A | 9/1996 | Henke |
| 5,609,627 A | 3/1997 | Goicoechea |
| 5,624,461 A | 4/1997 | Mariant |
| 5,639,277 A | 6/1997 | Mariant |
| 5,639,278 A | 6/1997 | Dereume et al. |
| 5,645,558 A | 7/1997 | Horton |
| 5,653,605 A | 8/1997 | Woehl et al. |
| 5,658,296 A | 8/1997 | Bates |
| 5,665,117 A | 9/1997 | Rhodes |
| 5,695,519 A | 12/1997 | Summer et al. |
| 5,709,704 A | 1/1998 | Nott et al. |
| 5,713,853 A | 2/1998 | Clark |
| 5,769,871 A | 6/1998 | Mers Kelly |
| 5,769,884 A | 6/1998 | Solovay |
| 5,779,686 A | 7/1998 | Sato et al. |
| 5,779,716 A | 7/1998 | Cano |
| 5,800,519 A | 9/1998 | Sandock |
| 5,810,874 A | 9/1998 | Lefebvre |
| 5,814,064 A | 9/1998 | Daniel |
| 5,827,304 A | 10/1998 | Hart |
| 5,853,422 A | 12/1998 | Huebsch et al. |
| 5,855,598 A | 1/1999 | Pinchuk |
| 5,893,869 A | 4/1999 | Barnhart et al. |
| 5,895,398 A | 4/1999 | Wensel |
| 5,897,567 A | 4/1999 | Ressemann |
| 5,904,698 A | 5/1999 | Thomas et al. |
| 5,911,702 A | 6/1999 | Romley |
| 5,911,725 A | 6/1999 | Boury |
| 5,919,126 A | 7/1999 | Armini |
| 5,931,509 A | 8/1999 | Bartholomew |
| 5,935,139 A | 8/1999 | Bates |
| 5,947,995 A | 9/1999 | Samuels |
| 6,063,113 A | 5/2000 | Kavteladze |
| 6,066,149 A | 5/2000 | Samson et al. |
| 6,066,158 A | 5/2000 | Engelson |
| 6,093,196 A | 7/2000 | Okada |
| 6,093,199 A | 7/2000 | Brown et al. |
| 6,096,053 A | 8/2000 | Bates |
| 6,099,534 A | 8/2000 | Bates |
| 6,099,559 A | 8/2000 | Nolting |
| 6,102,932 A | 8/2000 | Kurz |
| 6,106,548 A | 8/2000 | Roubin |
| 6,129,739 A | 10/2000 | Khosravi |
| 6,143,022 A | 11/2000 | Shull et al. |
| 6,146,404 A | 11/2000 | Kim |
| 6,156,064 A | 12/2000 | Chouinard |
| 6,165,194 A | 12/2000 | Denardo |
| 6,165,199 A | 12/2000 | Barbut |
| 6,168,604 B1 | 1/2001 | Cano |
| 6,168,622 B1 | 1/2001 | Mazzocchi |
| 6,174,318 B1 | 1/2001 | Bates et al. |
| 6,179,861 B1 | 1/2001 | Khosravi |
| 6,203,561 B1 | 3/2001 | Ramee |
| 6,214,026 B1 | 4/2001 | Lepak |
| 6,221,006 B1 | 4/2001 | Dubrul |
| 6,231,597 B1 | 5/2001 | Deem et al. |
| 6,238,412 B1 | 5/2001 | Dubrul |
| 6,245,012 B1 | 6/2001 | Kleshinski |
| 6,245,087 B1 | 6/2001 | Addis |
| 6,251,122 B1 | 6/2001 | Tsukernik |
| 6,254,571 B1 | 7/2001 | Hart |
| 6,264,663 B1 | 7/2001 | Cano |
| 6,267,777 B1 | 7/2001 | Bosma et al. |
| 6,290,710 B1 | 9/2001 | Cryer et al. |
| 6,312,444 B1 | 11/2001 | Barbut |
| 6,315,778 B1 | 11/2001 | Gambale |
| 6,325,815 B1 | 12/2001 | Kusleika |
| 6,325,819 B1 | 12/2001 | Pavcnik |
| 6,334,864 B1 | 1/2002 | Amplatz |
| 6,336,934 B1 | 1/2002 | Gilson et al. |
| 6,346,116 B1 | 2/2002 | Brooks |
| 6,348,056 B1 | 2/2002 | Bates |
| 6,350,271 B1 | 2/2002 | Kurz et al. |
| 6,355,057 B1 | 3/2002 | DeMarais et al. |
| 6,361,545 B1 | 3/2002 | Macoviak |
| 6,364,895 B1 | 4/2002 | Greenhalgh |
| 6,375,668 B1 | 4/2002 | Gifford |
| 6,375,670 B1 | 4/2002 | Greenhalgh |
| 6,383,205 B1 | 5/2002 | Samson et al. |
| 6,383,206 B1 | 5/2002 | Gillick |
| 6,391,037 B1 | 5/2002 | Greenhalgh |
| 6,402,771 B1 | 6/2002 | Palmer |
| 6,416,541 B2 | 7/2002 | Denardo |
| 6,425,909 B1 | 7/2002 | Dieck et al. |
| 6,428,558 B1 | 8/2002 | Jones |
| 6,432,122 B1 | 8/2002 | Gilson et al. |
| 6,436,112 B2 | 8/2002 | Wensel |
| 6,458,139 B1 | 10/2002 | Palmer |
| 6,485,497 B2 | 11/2002 | Wensel |
| 6,485,501 B1 | 11/2002 | Green |
| 6,485,502 B2 | 11/2002 | Don Michael |
| 6,488,701 B1 | 12/2002 | Nolting et al. |
| 6,511,492 B1 | 1/2003 | Rosenbluth |
| 6,530,935 B2 | 3/2003 | Wensel |
| 6,530,939 B1 | 3/2003 | Hopkins |
| 6,540,768 B1 | 4/2003 | Diaz et al. |
| 6,544,279 B1 | 4/2003 | Hopkins |
| 6,551,341 B2 | 4/2003 | Boylan et al. |
| 6,551,342 B1 | 4/2003 | Shen et al. |
| 6,575,996 B1 | 6/2003 | Denison |
| 6,575,997 B1 | 6/2003 | Palmer et al. |
| 6,582,448 B1 | 6/2003 | Boyle |
| 6,585,756 B1 | 7/2003 | Strecker |
| 6,589,265 B1 | 7/2003 | Palmer et al. |
| 6,592,607 B1 | 7/2003 | Palmer et al. |
| 6,592,614 B2 | 7/2003 | Lenker et al. |
| 6,592,616 B1 | 7/2003 | Stack |
| 6,598,265 B2 | 7/2003 | Lee |
| 6,602,265 B2 | 8/2003 | Dubrul |
| 6,602,271 B2 | 8/2003 | Adams |
| 6,602,272 B2 | 8/2003 | Boylan et al. |
| 6,605,102 B1 | 8/2003 | Mazzocchi |
| 6,610,077 B1 | 8/2003 | Hancock et al. |
| 6,616,679 B1 | 9/2003 | Khosravi |
| 6,632,241 B1 | 10/2003 | Hancock et al. |
| 6,638,245 B2 | 10/2003 | Miller |
| 6,638,293 B1 | 10/2003 | Makower et al. |
| 6,641,590 B1 | 11/2003 | Palmer et al. |
| 6,656,218 B1 | 12/2003 | Denardo et al. |
| 6,660,021 B1 | 12/2003 | Palmer |
| 6,663,650 B2 | 12/2003 | Sepetka |
| 6,673,089 B1 | 1/2004 | Yassour |
| 6,685,722 B1 | 2/2004 | Rosenbluth |
| 6,692,504 B2 | 2/2004 | Kurz et al. |
| 6,692,508 B2 | 2/2004 | Wensel |
| 6,692,509 B2 | 2/2004 | Wensel |
| 6,695,858 B1 | 2/2004 | Dubrul et al. |
| 6,702,782 B2 | 3/2004 | Miller |
| 6,712,834 B2 | 3/2004 | Yassour et al. |
| 6,726,701 B2 | 4/2004 | Gilson et al. |

(56) References Cited

U.S. PATENT DOCUMENTS

| | | |
|---|---|---|
| 6,726,703 B2 | 4/2004 | Broome |
| 6,730,104 B1 | 5/2004 | Sepetka |
| 6,783,528 B2 | 8/2004 | Vincent-Prestigiacomo |
| 6,783,538 B2 | 8/2004 | McGuckin, Jr. et al. |
| 6,824,545 B2 | 11/2004 | Sepetka |
| 6,855,155 B2 | 2/2005 | Denardo et al. |
| 6,878,163 B2 | 4/2005 | Denardo et al. |
| 6,890,340 B2 | 5/2005 | Duane |
| 6,913,612 B2 | 7/2005 | Palmer |
| 6,913,618 B2 | 7/2005 | Denardo et al. |
| 6,939,361 B1 | 9/2005 | Kleshinski |
| 6,953,472 B2 | 10/2005 | Palmer et al. |
| 6,989,019 B2 | 1/2006 | Mazzocchi |
| 6,989,021 B2 | 1/2006 | Bosma et al. |
| 6,994,718 B2 | 2/2006 | Groothuis et al. |
| 7,004,954 B1 | 2/2006 | Voss et al. |
| 7,004,955 B2 | 2/2006 | Shen |
| 7,004,956 B2 | 2/2006 | Palmer |
| 7,008,434 B2 | 3/2006 | Kurz et al. |
| 7,033,376 B2 | 4/2006 | Tsukernik |
| 7,041,116 B2 | 5/2006 | Goto |
| 7,048,758 B2 | 5/2006 | Boyle |
| 7,052,500 B2 | 5/2006 | Bashiri et al. |
| 7,058,456 B2 | 6/2006 | Pierce |
| 7,063,707 B2 | 6/2006 | Bose |
| 7,083,633 B2 | 8/2006 | Morrill et al. |
| 7,083,822 B2 | 8/2006 | Brightbill |
| 7,094,249 B1 | 8/2006 | Broome |
| 7,097,653 B2 | 8/2006 | Freudenthal |
| 7,101,380 B2 | 9/2006 | Khachin |
| 7,172,614 B2 | 2/2007 | Boyle et al. |
| 7,175,655 B1 | 2/2007 | Malaei |
| 7,179,273 B1 | 2/2007 | Palmer et al. |
| 7,185,922 B2 | 3/2007 | Takayanagi et al. |
| 7,220,271 B2 | 5/2007 | Clubb |
| 7,226,464 B2 | 6/2007 | Garner et al. |
| 7,229,472 B2 | 6/2007 | DePalma |
| 7,241,304 B2 | 7/2007 | Boyle et al. |
| 7,288,112 B2 | 10/2007 | Denardo et al. |
| 7,300,458 B2 | 11/2007 | Henkes et al. |
| 7,306,618 B2 | 12/2007 | Demond |
| 7,314,483 B2 | 1/2008 | Landau et al. |
| 7,316,692 B2 | 1/2008 | Huffmaster |
| 7,323,001 B2 | 1/2008 | Clubb |
| 7,331,976 B2 | 2/2008 | McGuckin, Jr |
| 7,344,550 B2 | 3/2008 | Carrison et al. |
| 7,399,308 B2 | 7/2008 | Borillo et al. |
| 7,410,491 B2 | 8/2008 | Hopkins |
| 7,425,215 B2 | 9/2008 | Boyle |
| 7,452,496 B2 | 11/2008 | Brady et al. |
| 7,491,215 B2 | 2/2009 | Vale |
| 7,491,216 B2 | 2/2009 | Brady |
| 7,510,565 B2 | 3/2009 | Gilson et al. |
| 7,534,252 B2 | 5/2009 | Sepetka |
| 7,556,636 B2 | 7/2009 | Mazzocchi |
| 7,582,111 B2 | 9/2009 | Krolik |
| 7,594,926 B2 | 9/2009 | Linder |
| 7,604,649 B2 | 10/2009 | McGuckin et al. |
| 7,604,650 B2 | 10/2009 | Bergheim |
| 7,609,649 B1 | 10/2009 | Bhandari et al. |
| 7,618,434 B2 | 11/2009 | Santra |
| 7,662,165 B2 | 2/2010 | Gilson et al. |
| 7,670,356 B2 | 3/2010 | Mazzocchi |
| 7,678,123 B2 | 3/2010 | Chanduszko |
| 7,691,121 B2 | 4/2010 | Rosenbluth |
| 7,691,124 B2 | 4/2010 | Balgobin |
| 7,708,770 B2 | 5/2010 | Linder |
| 7,717,929 B2 | 5/2010 | Fallman |
| 7,736,385 B2 | 6/2010 | Agnew |
| 7,758,606 B2 | 7/2010 | Streeter et al. |
| 7,758,611 B2 | 7/2010 | Kato |
| 7,766,934 B2 | 8/2010 | Pal |
| 7,771,452 B2 | 8/2010 | Pal |
| 7,780,694 B2 | 8/2010 | Palmer |
| 7,780,700 B2 | 8/2010 | Frazier et al. |
| 7,811,305 B2 | 10/2010 | Balgobin et al. |
| 7,815,659 B2 | 10/2010 | Conlon et al. |
| 7,819,893 B2 | 10/2010 | Brady |
| 7,828,815 B2 | 11/2010 | Mazzocchi |
| 7,828,816 B2 | 11/2010 | Mazzocchi et al. |
| 7,833,240 B2 | 11/2010 | Okushi et al. |
| 7,842,053 B2 | 11/2010 | Chanduszko et al. |
| 7,846,176 B2 | 11/2010 | Mazzocchi |
| 7,846,175 B2 | 12/2010 | Bonnette et al. |
| 7,850,708 B2 | 12/2010 | Pal |
| 7,883,516 B2 | 2/2011 | Huang et al. |
| 7,887,560 B2 | 2/2011 | Kusleika |
| 7,901,426 B2 | 3/2011 | Gilson et al. |
| 7,914,549 B2 | 3/2011 | Morsi |
| 7,922,732 B2 | 4/2011 | Mazzocchi |
| 7,927,784 B2 | 4/2011 | Simpson |
| 7,931,659 B2 | 4/2011 | Bose et al. |
| 7,998,165 B2 | 8/2011 | Huffmaster |
| 8,002,822 B2 | 8/2011 | Glocker et al. |
| 8,021,379 B2 | 9/2011 | Thompson et al. |
| 8,021,380 B2 | 9/2011 | Thompson et al. |
| 8,043,326 B2 | 10/2011 | Hancock et al. |
| 8,048,151 B2 | 11/2011 | O'Brien et al. |
| 8,052,640 B2 | 11/2011 | Fiorella et al. |
| 8,057,497 B1 | 11/2011 | Raju et al. |
| 8,057,507 B2 | 11/2011 | Horan |
| 8,066,757 B2 | 11/2011 | Ferrera et al. |
| 8,070,791 B2 | 12/2011 | Ferrera et al. |
| 8,088,140 B2 | 1/2012 | Ferrera |
| 8,100,935 B2 | 1/2012 | Rosenbluth et al. |
| 8,109,941 B2 | 2/2012 | Richardson |
| 8,118,829 B2 | 2/2012 | Carrison et al. |
| 8,118,856 B2 | 2/2012 | Schreck et al. |
| 8,123,769 B2 | 2/2012 | Osborne |
| 8,137,376 B2 | 3/2012 | Clubb et al. |
| 8,137,377 B2 | 3/2012 | Palmer et al. |
| 8,142,422 B2 | 3/2012 | Makower et al. |
| 8,142,442 B2 | 3/2012 | Palmer et al. |
| 8,182,508 B2 | 5/2012 | Magnuson et al. |
| 8,187,298 B2 | 5/2012 | Pal |
| 8,246,641 B2 | 8/2012 | Osborne et al. |
| 8,246,672 B2 | 8/2012 | Osborne |
| 8,252,017 B2 | 8/2012 | Paul, Jr. et al. |
| 8,252,018 B2 | 8/2012 | Valaie |
| 8,262,689 B2 | 9/2012 | Schneiderman |
| 8,282,668 B2 | 10/2012 | McGuckin, Jr. et al. |
| 8,287,538 B2 | 10/2012 | Brenzel et al. |
| 8,298,257 B2 | 10/2012 | Sepetka et al. |
| RE43,882 E | 12/2012 | Hopkins et al. |
| 8,357,178 B2 | 1/2013 | Grandfield et al. |
| 8,357,179 B2 | 1/2013 | Grandfield et al. |
| 8,357,180 B2 | 1/2013 | Feller, III |
| 8,357,893 B2 | 1/2013 | Xu et al. |
| 8,361,095 B2 | 1/2013 | Osborne |
| 8,361,110 B2 | 1/2013 | Chanduszko |
| 8,366,663 B2 | 2/2013 | Fiorella et al. |
| 8,409,215 B2 | 4/2013 | Sepetka et al. |
| 8,414,482 B2 | 4/2013 | Belson |
| 8,414,543 B2 | 4/2013 | McGuckin, Jr. |
| 8,419,748 B2 | 4/2013 | Valaie |
| 8,460,312 B2 | 6/2013 | Bose et al. |
| 8,460,313 B2 | 6/2013 | Huffmaster |
| 8,486,104 B2 | 7/2013 | Samson et al. |
| 8,512,352 B2 | 8/2013 | Martin |
| 8,529,596 B2 | 9/2013 | Grandfield et al. |
| 8,545,526 B2 | 10/2013 | Martin et al. |
| 8,574,262 B2 | 11/2013 | Ferrera et al. |
| 8,574,915 B2 | 11/2013 | Zhang et al. |
| 8,579,915 B2 | 11/2013 | French et al. |
| 8,585,713 B2 | 11/2013 | Ferrera et al. |
| 8,608,761 B2 | 12/2013 | Osborne et al. |
| 8,679,142 B2 | 3/2014 | Slee et al. |
| 8,690,907 B1 | 4/2014 | Janardhan et al. |
| 8,696,622 B2 | 4/2014 | Fiorella et al. |
| 8,702,652 B2 | 4/2014 | Fiorella et al. |
| 8,702,704 B2 | 4/2014 | Shelton, IV et al. |
| 8,702,724 B2 | 4/2014 | Olsen et al. |
| 8,777,919 B2 | 7/2014 | Kimura et al. |
| 8,777,976 B2 | 7/2014 | Brady et al. |

(56) References Cited

U.S. PATENT DOCUMENTS

| | | |
|---|---|---|
| 8,777,979 B2 | 7/2014 | Shrivastava et al. |
| 8,784,434 B2 | 7/2014 | Rosenbluth et al. |
| 8,784,441 B2 | 7/2014 | Rosenbluth et al. |
| 8,795,305 B2 | 8/2014 | Grandfield et al. |
| 8,795,317 B2 | 8/2014 | Grandfield et al. |
| 8,795,345 B2 | 8/2014 | Grandfield et al. |
| 8,814,892 B2 | 8/2014 | Galdonik et al. |
| 8,814,925 B2 | 8/2014 | Hilaire et al. |
| 8,852,205 B2 | 10/2014 | Brady et al. |
| 8,870,941 B2 | 10/2014 | Evans et al. |
| 8,900,265 B1 | 12/2014 | Ulm, III |
| 8,920,358 B2 | 12/2014 | Levine et al. |
| 8,939,991 B2 | 1/2015 | Krolick et al. |
| 8,945,143 B2 | 2/2015 | Ferrera et al. |
| 8,945,160 B2 | 2/2015 | Krolik et al. |
| 8,945,169 B2 | 2/2015 | Pal |
| 8,945,172 B2 | 2/2015 | Ferrera et al. |
| 8,956,399 B2 | 2/2015 | Cam et al. |
| 8,968,330 B2 | 3/2015 | Rosenbluth et al. |
| 9,011,481 B2 | 4/2015 | Aggerholm et al. |
| 9,039,749 B2 | 5/2015 | Shrivastava et al. |
| 9,072,537 B2 | 7/2015 | Grandfield |
| 9,095,342 B2 | 8/2015 | Becking et al. |
| 9,113,936 B2 | 8/2015 | Palmer et al. |
| 9,119,656 B2 | 9/2015 | Bose et al. |
| 9,138,307 B2 | 9/2015 | Valaie |
| 9,155,552 B2 | 10/2015 | Ulm, III |
| 9,161,758 B2 | 10/2015 | Figulla |
| 9,161,766 B2 | 10/2015 | Slee et al. |
| 9,173,668 B2 | 11/2015 | Ulm, III |
| 9,173,688 B2 | 11/2015 | Dosta |
| 9,186,487 B2 | 11/2015 | Dubrul et al. |
| 9,198,687 B2 | 12/2015 | Fulkerson et al. |
| 9,204,887 B2 | 12/2015 | Cully et al. |
| 9,221,132 B2 | 12/2015 | Bowman |
| 9,232,992 B2 | 1/2016 | Heidner |
| 9,254,371 B2 | 2/2016 | Martin et al. |
| 9,301,769 B2 | 4/2016 | Brady et al. |
| 9,332,999 B2 | 5/2016 | Ray et al. |
| 9,402,707 B2 | 8/2016 | Brady et al. |
| 9,445,829 B2 | 9/2016 | Brady et al. |
| 9,456,834 B2 | 10/2016 | Folk |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,104 B2 | 2/2017 | Beckham et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,639 B2 | 5/2017 | Brady et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,898 B2 | 5/2017 | Palepu et al. |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,758,606 B2 | 9/2017 | Lambert et al. |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Paterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,304 B2 | 12/2017 | Horan |
| 9,833,604 B2 | 12/2017 | Lam et al. |
| 9,833,625 B2 | 12/2017 | Waldhauser et al. |
| 9,901,434 B2 | 2/2018 | Hoffman |
| 9,918,720 B2 | 3/2018 | Marchand et al. |
| 9,939,361 B2 | 4/2018 | Gajji et al. |
| 10,070,878 B2 | 9/2018 | Ma |
| 10,201,360 B2 | 2/2019 | Vale et al. |
| 10,237,751 B2 | 3/2019 | Morioka |
| 10,292,723 B2 | 5/2019 | Brady et al. |
| 10,299,811 B2 | 5/2019 | Brady et al. |
| 10,363,054 B2 | 7/2019 | Vale et al. |
| 10,376,274 B2 | 8/2019 | Farin et al. |
| 10,390,850 B2 | 8/2019 | Vale et al. |
| 10,524,811 B2 | 1/2020 | Marchand et al. |
| 10,617,435 B2 | 4/2020 | Vale et al. |
| 10,722,257 B2 | 7/2020 | Skillrud et al. |
| 2001/0001315 A1 | 5/2001 | Bates |
| 2001/0016755 A1 | 8/2001 | Addis |
| 2001/0037141 A1 | 11/2001 | Yee et al. |
| 2001/0037171 A1 | 11/2001 | Sato |
| 2001/0041909 A1 | 11/2001 | Tsugita et al. |
| 2001/0049554 A1 | 12/2001 | Ruiz et al. |
| 2001/0051810 A1 | 12/2001 | Dubrul |
| 2002/0004667 A1 | 1/2002 | Adams |
| 2002/0016609 A1 | 2/2002 | Wensel |
| 2002/0022859 A1 | 2/2002 | Hogendijk |
| 2002/0026211 A1 | 2/2002 | Khosravi |
| 2002/0042627 A1 | 4/2002 | Brady et al. |
| 2002/0049468 A1 | 4/2002 | Streeter |
| 2002/0052620 A1 | 5/2002 | Barbut |
| 2002/0058911 A1 | 5/2002 | Gilson et al. |
| 2002/0068954 A1 | 6/2002 | Foster |
| 2002/0072764 A1 | 6/2002 | Sepetka |
| 2002/0082558 A1 | 6/2002 | Samson |
| 2002/0091407 A1 | 7/2002 | Zadno-Azizi et al. |
| 2002/0095171 A1 | 7/2002 | Belef |
| 2002/0123765 A1 | 9/2002 | Sepetka |
| 2002/0138094 A1 | 9/2002 | Borillo et al. |
| 2002/0143349 A1 | 10/2002 | Gifford, III et al. |
| 2002/0143362 A1 | 10/2002 | Macoviak |
| 2002/0156455 A1 | 10/2002 | Barbut |
| 2002/0161393 A1 | 10/2002 | Demond |
| 2002/0165576 A1 | 11/2002 | Boyle et al. |
| 2002/0173819 A1 | 11/2002 | Leeflang et al. |
| 2002/0183787 A1 | 12/2002 | Wahr et al. |
| 2002/0188276 A1 | 12/2002 | Evans |
| 2002/0188314 A1 | 12/2002 | Anderson et al. |
| 2002/0193824 A1 | 12/2002 | Boylan et al. |
| 2002/0198588 A1 | 12/2002 | Armstrong et al. |
| 2003/0004536 A1 | 1/2003 | Boylan |
| 2003/0004538 A1 | 1/2003 | Secrest |
| 2003/0004540 A1 | 1/2003 | Linder |
| 2003/0004542 A1 | 1/2003 | Wensel |
| 2003/0009146 A1 | 1/2003 | Muni |
| 2003/0009191 A1 | 1/2003 | Wensel |
| 2003/0038447 A1 | 2/2003 | Cantele |

(56) References Cited

U.S. PATENT DOCUMENTS

| | | |
|---|---|---|
| 2003/0040772 A1 | 2/2003 | Hyodoh |
| 2003/0050663 A1 | 3/2003 | Khachin |
| 2003/0064151 A1 | 4/2003 | Klinedinst |
| 2003/0108224 A1 | 6/2003 | Ike |
| 2003/0114879 A1 | 6/2003 | Euteneuer |
| 2003/0125798 A1 | 7/2003 | Martin |
| 2003/0130682 A1 | 7/2003 | Broome |
| 2003/0144687 A1 | 7/2003 | Brady et al. |
| 2003/0144688 A1 | 7/2003 | Brady et al. |
| 2003/0153158 A1 | 8/2003 | Ho et al. |
| 2003/0153943 A1 | 8/2003 | Michael |
| 2003/0153944 A1 | 8/2003 | Phung |
| 2003/0163064 A1 | 8/2003 | Vrba |
| 2003/0163158 A1 | 8/2003 | White |
| 2003/0171769 A1 | 9/2003 | Barbut |
| 2003/0171771 A1 | 9/2003 | Anderson et al. |
| 2003/0176884 A1 | 9/2003 | Berrada |
| 2003/0187495 A1 | 10/2003 | Cully et al. |
| 2003/0195537 A1 | 10/2003 | Dubrul |
| 2003/0195554 A1 | 10/2003 | Shen |
| 2003/0199917 A1 | 10/2003 | Knudson |
| 2003/0204202 A1 | 10/2003 | Palmer |
| 2003/0208224 A1 | 11/2003 | Broome |
| 2003/0212430 A1 | 11/2003 | Bose |
| 2003/0236533 A1 | 12/2003 | Wilson |
| 2004/0064179 A1 | 4/2004 | Linder et al. |
| 2004/0068288 A1 | 4/2004 | Palmer et al. |
| 2004/0073243 A1 | 4/2004 | Sepetka |
| 2004/0079429 A1 | 4/2004 | Miller |
| 2004/0082962 A1 | 4/2004 | Demarais et al. |
| 2004/0082967 A1 | 4/2004 | Broome et al. |
| 2004/0088001 A1 | 5/2004 | Bosma |
| 2004/0093065 A1 | 5/2004 | Yachia |
| 2004/0098050 A1 | 5/2004 | Foerster et al. |
| 2004/0133231 A1 | 7/2004 | Maitland |
| 2004/0133232 A1 | 7/2004 | Rosenbluth et al. |
| 2004/0138692 A1 | 7/2004 | Phung |
| 2004/0153117 A1 | 8/2004 | Clubb et al. |
| 2004/0153118 A1 | 8/2004 | Clubb |
| 2004/0199201 A1 | 10/2004 | Kellett et al. |
| 2004/0215318 A1 | 10/2004 | Kwitkin |
| 2004/0220663 A1 | 11/2004 | Rivelli |
| 2005/0033248 A1 | 2/2005 | Machida et al. |
| 2005/0033348 A1 | 2/2005 | Sepetka |
| 2005/0038447 A1 | 2/2005 | Huffmaster |
| 2005/0038468 A1 | 2/2005 | Panetta |
| 2005/0043759 A1 | 2/2005 | Chanduszko |
| 2005/0049619 A1 | 3/2005 | Sepetka |
| 2005/0049669 A1 | 3/2005 | Jones |
| 2005/0049670 A1 | 3/2005 | Jones et al. |
| 2005/0055033 A1 | 3/2005 | Leslie et al. |
| 2005/0055047 A1 | 3/2005 | Greenhalgh |
| 2005/0058837 A1 | 3/2005 | Farnworth et al. |
| 2005/0059995 A1 | 3/2005 | Sepetka |
| 2005/0085849 A1 | 4/2005 | Sepetka |
| 2005/0090779 A1 | 4/2005 | Osypka |
| 2005/0090857 A1 | 4/2005 | Kusleika et al. |
| 2005/0125024 A1 | 6/2005 | Sepetka |
| 2005/0149997 A1 | 7/2005 | Wolozin et al. |
| 2005/0171566 A1 | 8/2005 | Kanamaru |
| 2005/0173135 A1 | 8/2005 | Almen |
| 2005/0192627 A1 | 9/2005 | Whisenant et al. |
| 2005/0216030 A1 | 9/2005 | Sepetka |
| 2005/0216050 A1 | 9/2005 | Sepetka |
| 2005/0228417 A1 | 10/2005 | Teitelbaum et al. |
| 2005/0251206 A1 | 11/2005 | Maahs et al. |
| 2005/0251209 A1 | 11/2005 | Saadat et al. |
| 2005/0267491 A1 | 12/2005 | Kellett et al. |
| 2005/0273135 A1 | 12/2005 | Chanduszko et al. |
| 2005/0283186 A1 | 12/2005 | Berrada et al. |
| 2005/0288686 A1 | 12/2005 | Sepetka |
| 2006/0008332 A1 | 1/2006 | Greenberg et al. |
| 2006/0009798 A1 | 1/2006 | Callister et al. |
| 2006/0009799 A1 | 1/2006 | Kleshinski |
| 2006/0020286 A1 | 1/2006 | Niermann |
| 2006/0030877 A1 | 2/2006 | Martinez |
| 2006/0041228 A1 | 2/2006 | Vo et al. |
| 2006/0058836 A1 | 3/2006 | Bose |
| 2006/0058837 A1 | 3/2006 | Bose et al. |
| 2006/0058838 A1 | 3/2006 | Bose |
| 2006/0064151 A1 | 3/2006 | Guterman |
| 2006/0069424 A1 | 3/2006 | Acosta et al. |
| 2006/0074477 A1 | 4/2006 | Berthiaume et al. |
| 2006/0149313 A1 | 7/2006 | Arguello et al. |
| 2006/0155305 A1 | 7/2006 | Freudenthal |
| 2006/0161187 A1 | 7/2006 | Levine |
| 2006/0195137 A1 | 8/2006 | Sepetka |
| 2006/0224177 A1 | 10/2006 | Finitsis |
| 2006/0224179 A1 | 10/2006 | Kucharczyk |
| 2006/0229638 A1 | 10/2006 | Abrams et al. |
| 2006/0235501 A1 | 10/2006 | Igaki |
| 2006/0241677 A1 | 10/2006 | Johnson et al. |
| 2006/0282111 A1 | 12/2006 | Morsi |
| 2006/0287668 A1 | 12/2006 | Fawzi et al. |
| 2006/0287701 A1 | 12/2006 | Pal |
| 2006/0293706 A1 | 12/2006 | Shimon |
| 2007/0010857 A1 | 1/2007 | Sugimoto et al. |
| 2007/0032879 A1 | 2/2007 | Levine et al. |
| 2007/0088382 A1 | 4/2007 | Bei et al. |
| 2007/0088383 A1 | 4/2007 | Pal et al. |
| 2007/0100348 A1 | 5/2007 | Cauthen et al. |
| 2007/0118173 A1 | 5/2007 | Magnuson et al. |
| 2007/0149997 A1 | 6/2007 | Muller |
| 2007/0156170 A1 | 7/2007 | Hancock |
| 2007/0165170 A1 | 7/2007 | Fukuda |
| 2007/0179527 A1 | 8/2007 | Eskuri et al. |
| 2007/0191866 A1 | 8/2007 | Palmer et al. |
| 2007/0198028 A1 | 8/2007 | Miloslavski |
| 2007/0198051 A1 | 8/2007 | Clubb et al. |
| 2007/0198075 A1 | 8/2007 | Levy |
| 2007/0208367 A1 | 9/2007 | Fiorella |
| 2007/0208371 A1 | 9/2007 | French |
| 2007/0225749 A1 | 9/2007 | Martin |
| 2007/0233175 A1 | 10/2007 | Zaver et al. |
| 2007/0244505 A1 | 10/2007 | Gilson et al. |
| 2007/0270902 A1 | 11/2007 | Slazas |
| 2007/0288054 A1 | 12/2007 | Tanaka |
| 2008/0045881 A1 | 2/2008 | Teitelbaum et al. |
| 2008/0077227 A1 | 3/2008 | Ouellette et al. |
| 2008/0082107 A1 | 4/2008 | Miller et al. |
| 2008/0086190 A1 | 4/2008 | Ta |
| 2008/0091223 A1 | 4/2008 | Pokorney |
| 2008/0097386 A1 | 4/2008 | Osypka |
| 2008/0109031 A1 | 5/2008 | Sepetka |
| 2008/0109032 A1 | 5/2008 | Sepetka |
| 2008/0119886 A1 | 5/2008 | Greenhalgh et al. |
| 2008/0177296 A1 | 7/2008 | Sepetka |
| 2008/0178890 A1 | 7/2008 | Townsend et al. |
| 2008/0183197 A1 | 7/2008 | Sepetka |
| 2008/0183198 A1 | 7/2008 | Sepetka |
| 2008/0183205 A1 | 7/2008 | Sepetka |
| 2008/0188876 A1 | 8/2008 | Sepetka |
| 2008/0188885 A1 | 8/2008 | Sepetka |
| 2008/0188887 A1 | 8/2008 | Batiste |
| 2008/0200946 A1 | 8/2008 | Braun |
| 2008/0200947 A1 | 8/2008 | Kusleika et al. |
| 2008/0215077 A1 | 9/2008 | Sepetka |
| 2008/0221600 A1 | 9/2008 | Dieck |
| 2008/0228209 A1 | 9/2008 | DeMello et al. |
| 2008/0234706 A1 | 9/2008 | Sepetka |
| 2008/0243170 A1 | 10/2008 | Jenson |
| 2008/0255596 A1 | 10/2008 | Jenson |
| 2008/0262410 A1 | 10/2008 | Jenson et al. |
| 2008/0262528 A1 | 10/2008 | Martin |
| 2008/0262532 A1 | 10/2008 | Martin |
| 2008/0269871 A1 | 10/2008 | Eli |
| 2008/0275488 A1 | 11/2008 | Fleming |
| 2008/0275493 A1 | 11/2008 | Farmiga |
| 2008/0281350 A1 | 11/2008 | Sepetka |
| 2008/0312681 A1 | 12/2008 | Ansel |
| 2009/0005858 A1 | 1/2009 | Young et al. |
| 2009/0024157 A1 | 1/2009 | Anukhin |
| 2009/0030443 A1 | 1/2009 | Buser et al. |
| 2009/0062841 A1 | 3/2009 | Amplatz et al. |

(56) References Cited

U.S. PATENT DOCUMENTS

| | | |
|---|---|---|
| 2009/0069828 A1 | 3/2009 | Martin |
| 2009/0076539 A1 | 3/2009 | Valaie |
| 2009/0088793 A1 | 4/2009 | Bagaoisan et al. |
| 2009/0088795 A1 | 4/2009 | Cahill |
| 2009/0105722 A1 | 4/2009 | Fulkerson |
| 2009/0105737 A1 | 4/2009 | Fulkerson |
| 2009/0105747 A1 | 4/2009 | Chanduszko et al. |
| 2009/0149881 A1 | 6/2009 | Vale et al. |
| 2009/0163851 A1 | 6/2009 | Holloway et al. |
| 2009/0177206 A1 | 7/2009 | Lozier |
| 2009/0182336 A1 | 7/2009 | Brenzel |
| 2009/0281610 A1 | 11/2009 | Parker |
| 2009/0281619 A1 | 11/2009 | Le et al. |
| 2009/0292297 A1 | 11/2009 | Ferrere |
| 2009/0292307 A1 | 11/2009 | Razack |
| 2009/0299393 A1 | 12/2009 | Martin |
| 2009/0299403 A1 | 12/2009 | Chanduszko |
| 2009/0306702 A1 | 12/2009 | Miloslavski |
| 2009/0326636 A1 | 12/2009 | Hashimoto et al. |
| 2010/0004607 A1 | 1/2010 | Wilson et al. |
| 2010/0076482 A1 | 3/2010 | Shu et al. |
| 2010/0087850 A1 | 4/2010 | Razack |
| 2010/0087908 A1 | 4/2010 | Hilaire |
| 2010/0114017 A1 | 5/2010 | Lenker |
| 2010/0125326 A1 | 5/2010 | Kalstad |
| 2010/0125327 A1 | 5/2010 | Agnew |
| 2010/0191272 A1 | 7/2010 | Keating |
| 2010/0211094 A1 | 8/2010 | Sargent, Jr. |
| 2010/0268264 A1 | 10/2010 | Bonnett et al. |
| 2010/0268265 A1 | 10/2010 | Krolik et al. |
| 2010/0274277 A1 | 10/2010 | Eaton |
| 2010/0318178 A1 | 12/2010 | Rapaport et al. |
| 2010/0324649 A1 | 12/2010 | Mattsson |
| 2010/0331949 A1 | 12/2010 | Habib |
| 2011/0009875 A1 | 1/2011 | Grandfield et al. |
| 2011/0009940 A1 | 1/2011 | Grandfield |
| 2011/0009950 A1 | 1/2011 | Grandfield et al. |
| 2011/0022149 A1 | 1/2011 | Cox |
| 2011/0040319 A1 | 2/2011 | Fulton, III |
| 2011/0054514 A1 | 3/2011 | Arcand |
| 2011/0054516 A1 | 3/2011 | Keegan |
| 2011/0060212 A1 | 3/2011 | Slee et al. |
| 2011/0060359 A1 | 3/2011 | Hannes |
| 2011/0054504 A1 | 5/2011 | Wolf et al. |
| 2011/0106137 A1 | 5/2011 | Shimon |
| 2011/0125181 A1 | 5/2011 | Brady et al. |
| 2011/0152920 A1 | 6/2011 | Eckhouse et al. |
| 2011/0160763 A1 | 6/2011 | Ferrera |
| 2011/0166586 A1 | 7/2011 | Sepetka et al. |
| 2011/0184456 A1 | 7/2011 | Grandfield et al. |
| 2011/0196414 A1 | 8/2011 | Porter et al. |
| 2011/0202088 A1 | 8/2011 | Eckhouse et al. |
| 2011/0208233 A1 | 8/2011 | McGuckin, Jr. et al. |
| 2011/0213297 A1 | 9/2011 | Aklog et al. |
| 2011/0213393 A1 | 9/2011 | Aklog et al. |
| 2011/0213403 A1 | 9/2011 | Aboytes |
| 2011/0224707 A1 | 9/2011 | Miloslavski |
| 2011/0276120 A1 | 11/2011 | Gilson et al. |
| 2011/0319917 A1 | 12/2011 | Ferrera et al. |
| 2012/0041449 A1 | 2/2012 | Eckhouse et al. |
| 2012/0041474 A1 | 2/2012 | Eckhouse et al. |
| 2012/0059356 A1 | 3/2012 | diPalma et al. |
| 2012/0065660 A1 | 3/2012 | Ferrera et al. |
| 2012/0083823 A1 | 4/2012 | Shrivastava |
| 2012/0083868 A1 | 4/2012 | Shrivastava et al. |
| 2012/0089216 A1 | 4/2012 | Rapaport et al. |
| 2012/0101510 A1 | 4/2012 | Lenker et al. |
| 2012/0123466 A1 | 5/2012 | Porter et al. |
| 2012/0022572 A1 | 6/2012 | Braun et al. |
| 2012/0150147 A1 | 6/2012 | Leynov et al. |
| 2012/0165858 A1 | 6/2012 | Eckhouse et al. |
| 2012/0165859 A1 | 6/2012 | Eckhouse et al. |
| 2012/0296362 A1 | 6/2012 | Cam |
| 2012/0209312 A1 | 8/2012 | Aggerholm et al. |
| 2012/0215250 A1 | 8/2012 | Grandfield et al. |
| 2012/0143237 A1 | 11/2012 | Cam |
| 2012/0277788 A1 | 11/2012 | Cattaneo |
| 2012/0283768 A1 | 11/2012 | Cox et al. |
| 2012/0316600 A1 | 12/2012 | Ferrera et al. |
| 2012/0330350 A1 | 12/2012 | Jones et al. |
| 2013/0030460 A1 | 1/2013 | Marks et al. |
| 2013/0030461 A1 | 1/2013 | Marks et al. |
| 2013/0046330 A1 | 2/2013 | McIntosh |
| 2013/0046333 A1 | 2/2013 | Jones et al. |
| 2013/0046334 A1 | 2/2013 | Jones et al. |
| 2013/0116774 A1 | 5/2013 | Strauss |
| 2013/0131614 A1 | 5/2013 | Hassan et al. |
| 2013/0144311 A1 | 6/2013 | Fung et al. |
| 2013/0144326 A1 | 6/2013 | Brady et al. |
| 2013/0158592 A1 | 6/2013 | Porter |
| 2013/0184739 A1 | 7/2013 | Brady et al. |
| 2013/0197567 A1 | 8/2013 | Brady et al. |
| 2013/0226146 A1 | 8/2013 | Tekulve |
| 2013/0268050 A1 | 10/2013 | Wilson et al. |
| 2013/0271788 A1 | 10/2013 | Utsunomiya |
| 2013/0277079 A1 | 10/2013 | Tsuzuki et al. |
| 2013/0281788 A1 | 10/2013 | Garrison |
| 2013/0325051 A1 | 12/2013 | Martin et al. |
| 2013/0325055 A1 | 12/2013 | Eckhouse et al. |
| 2013/0325056 A1 | 12/2013 | Eckhouse et al. |
| 2013/0345739 A1 | 12/2013 | Brady et al. |
| 2014/0005712 A1 | 1/2014 | Martin |
| 2014/0005713 A1 | 1/2014 | Bowman |
| 2014/0046359 A1 | 2/2014 | Bowman et al. |
| 2014/0121672 A1 | 5/2014 | Folk |
| 2014/0128905 A1 | 5/2014 | Molaei |
| 2014/0134654 A1 | 5/2014 | Rudel et al. |
| 2014/0135812 A1 | 5/2014 | Divino et al. |
| 2014/0142598 A1 | 5/2014 | Fulton, III |
| 2014/0180377 A1 | 6/2014 | Bose et al. |
| 2014/0180397 A1 | 6/2014 | Gerberding et al. |
| 2014/0183077 A1 | 7/2014 | Rosendall et al. |
| 2014/0194911 A1 | 7/2014 | Johnson et al. |
| 2014/0194919 A1 | 7/2014 | Losardo et al. |
| 2014/0200607 A1 | 7/2014 | Sepetka et al. |
| 2014/0200608 A1 | 7/2014 | Brady et al. |
| 2014/0236220 A1 | 8/2014 | Inoue |
| 2014/0243881 A1 | 8/2014 | Lees et al. |
| 2014/0257362 A1 | 9/2014 | Eidenschink |
| 2014/0276922 A1 | 9/2014 | McLain et al. |
| 2014/0277079 A1 | 9/2014 | Vale et al. |
| 2014/0303667 A1 | 10/2014 | Cox et al. |
| 2014/0309657 A1 | 10/2014 | Ben-Ami |
| 2014/0309673 A1 | 10/2014 | Dacuycuy et al. |
| 2014/0330302 A1 | 11/2014 | Tekulve et al. |
| 2014/0343585 A1 | 11/2014 | Ferrera et al. |
| 2014/0371769 A1 | 12/2014 | Vale et al. |
| 2014/0371779 A1 | 12/2014 | Vale et al. |
| 2014/0371780 A1 | 12/2014 | Vale et al. |
| 2014/0372779 A1 | 12/2014 | Wong et al. |
| 2014/0379023 A1 | 12/2014 | Brady et al. |
| 2015/0018859 A1 | 1/2015 | Quick et al. |
| 2015/0018860 A1 | 1/2015 | Quick et al. |
| 2015/0032144 A1 | 1/2015 | Holloway |
| 2015/0080937 A1 | 3/2015 | Davidson |
| 2015/0112376 A1 | 4/2015 | Molaei et al. |
| 2015/0133990 A1 | 5/2015 | Davidson |
| 2015/0150672 A1 | 6/2015 | Ma |
| 2015/0164523 A1 | 6/2015 | Brady et al. |
| 2015/0224133 A1 | 8/2015 | Ohri et al. |
| 2015/0250497 A1 | 9/2015 | Marks et al. |
| 2015/0257775 A1 | 9/2015 | Gilvarry et al. |
| 2015/0272716 A1 | 10/2015 | Pinchuk et al. |
| 2015/0297252 A1 | 10/2015 | Miloslavski et al. |
| 2015/0313617 A1 | 11/2015 | Grandfield et al. |
| 2015/0320431 A1 | 11/2015 | Ulm, III |
| 2015/0352325 A1 | 12/2015 | Quick |
| 2015/0359547 A1 | 12/2015 | Vale et al. |
| 2015/0366650 A1 | 12/2015 | Zi et al. |
| 2015/0374391 A1 | 12/2015 | Quick et al. |
| 2015/0374393 A1 | 12/2015 | Brady et al. |
| 2015/0374479 A1 | 12/2015 | Vale |
| 2016/0015402 A1 | 1/2016 | Brady et al. |
| 2016/0022269 A1 | 1/2016 | Ganske et al. |

(56) References Cited

U.S. PATENT DOCUMENTS

| | | |
|---|---|---|
| 2016/0022296 A1 | 1/2016 | Brady et al. |
| 2016/0045298 A1 | 2/2016 | Thinnes, Jr. et al. |
| 2016/0066921 A1 | 3/2016 | Brady et al. |
| 2016/0100928 A1 | 4/2016 | Lees et al. |
| 2016/0106448 A1 | 4/2016 | Seifert et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0120558 A1 | 5/2016 | Brady et al. |
| 2016/0143653 A1 | 5/2016 | Vale et al. |
| 2016/0192953 A1 | 7/2016 | Brady et al. |
| 2016/0192954 A1 | 7/2016 | Brady et al. |
| 2016/0192955 A1 | 7/2016 | Brady et al. |
| 2016/0192956 A1 | 7/2016 | Brady et al. |
| 2016/0256180 A1 | 9/2016 | Vale et al. |
| 2016/0303381 A1 | 10/2016 | Pierce et al. |
| 2016/0317168 A1 | 11/2016 | Vale et al. |
| 2017/0007264 A1 | 1/2017 | Cruise et al. |
| 2017/0007265 A1 | 1/2017 | Guo et al. |
| 2017/0020542 A1 | 1/2017 | Martin et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0056061 A1 | 3/2017 | Ogle et al. |
| 2017/0071614 A1 | 3/2017 | Vale et al. |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086862 A1 | 3/2017 | Vale et al. |
| 2017/0086863 A1 | 3/2017 | Brady et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0105743 A1 | 4/2017 | Vale et al. |
| 2017/0112515 A1 | 4/2017 | Brady et al. |
| 2017/0112647 A1 | 4/2017 | Sachar et al. |
| 2017/0113023 A1 | 4/2017 | Steingisser et al. |
| 2017/0119409 A1 | 5/2017 | Ma |
| 2017/0143465 A1 | 5/2017 | Ulm, III |
| 2017/0147765 A1 | 5/2017 | Mehta |
| 2017/0150979 A1 | 6/2017 | John |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0055884 A1 | 3/2018 | Barclay Dupere et al. |
| 2018/0263650 A1 | 9/2018 | Iwanami et al. |
| 2018/0325537 A1 | 11/2018 | Shamay et al. |
| 2018/0326024 A1 | 11/2018 | Prochazka et al. |
| 2018/0344338 A1 | 12/2018 | Brady et al. |
| 2019/0000492 A1 | 1/2019 | Casey et al. |
| 2019/0015061 A1 | 1/2019 | Liebskind et al. |
| 2019/0167284 A1 | 6/2019 | Friedman et al. |
| 2019/0239907 A1 | 8/2019 | Brady et al. |
| 2019/0292273 A1 | 9/2019 | Hanotin et al. |
| 2019/0374239 A1 | 12/2019 | Martin et al. |
| 2019/0380723 A1 | 12/2019 | Grandfield et al. |
| 2019/0388097 A1 | 12/2019 | Girdhar et al. |
| 2020/0009150 A1 | 1/2020 | Chamorro Sanchez |
| 2020/0100804 A1 | 4/2020 | Casey et al. |

FOREIGN PATENT DOCUMENTS

| | | |
|---|---|---|
| CN | 102307613 A | 1/2012 |
| CN | 102596098 A | 7/2012 |
| CN | 103764049 A | 4/2014 |
| CN | 104042304 A | 9/2014 |
| CN | 105208950 A | 12/2015 |
| CN | 105662532 A | 6/2016 |
| CN | 205359559 U | 7/2016 |
| CN | 107530090 A | 1/2018 |
| CN | 208582467 U | 3/2019 |
| DE | 202009001951 U1 | 4/2010 |
| DE | 102009056450 | 6/2011 |
| DE | 102010010849 | 9/2011 |
| DE | 10 2010 014778 A1 | 10/2011 |
| DE | 102010024085 | 12/2011 |
| DE | 102011014586 B3 | 9/2012 |
| EP | 1153581 A1 | 11/2011 |
| EP | 2301450 B1 | 11/2011 |
| EP | 2438891 A1 | 4/2012 |
| EP | 2628455 A1 | 8/2013 |
| EP | 3156004 A1 | 4/2017 |
| GB | 2427554 A | 1/2007 |
| GB | 2494820 A | 3/2013 |
| JP | 9-19438 A | 1/1997 |
| JP | 2014511223 A | 5/2014 |
| JP | 2014525796 A | 10/2014 |
| JP | 2019-526365 A | 5/2016 |
| JP | 2016-513505 A | 9/2019 |
| WO | 94/24926 | 11/1994 |
| WO | 97/27808 | 8/1997 |
| WO | 97/38631 A1 | 10/1997 |
| WO | 99/20335 | 4/1999 |
| WO | 99/60933 | 12/1999 |

(56) References Cited

FOREIGN PATENT DOCUMENTS

| | | |
|---|---|---|
| WO | 99/56801 | 4/2000 |
| WO | 01/21077 | 3/2001 |
| WO | 2004/056275 A1 | 7/2001 |
| WO | 02/02162 | 1/2002 |
| WO | 02/11627 | 2/2002 |
| WO | 02/43616 | 6/2002 |
| WO | 02/070061 | 9/2002 |
| WO | 02/094111 | 11/2002 |
| WO | 03/002006 | 1/2003 |
| WO | 03/030751 | 4/2003 |
| WO | 03/051448 | 6/2003 |
| WO | 2004/028571 A2 | 4/2004 |
| WO | 2005/000130 A1 | 1/2005 |
| WO | 2005/027779 A2 | 3/2005 |
| WO | 2006/021407 | 3/2006 |
| WO | 2006/031410 | 3/2006 |
| WO | 2006/107641 | 10/2006 |
| WO | 2006/135823 A2 | 12/2006 |
| WO | 2007/054307 | 5/2007 |
| WO | 2007/068424 | 6/2007 |
| WO | 2008/034615 | 3/2008 |
| WO | 2008/051431 A1 | 5/2008 |
| WO | 2008/131116 | 10/2008 |
| WO | 2008135823 A1 | 11/2008 |
| WO | 2009/031338 A1 | 3/2009 |
| WO | 2009/076482 | 6/2009 |
| WO | 2009/086482 | 7/2009 |
| WO | 2009/105710 A1 | 8/2009 |
| WO | 2010/010545 | 1/2010 |
| WO | 201 0/046897 A1 | 4/2010 |
| WO | 2010/075565 A2 | 7/2010 |
| WO | 2010/102307 A1 | 9/2010 |
| WO | 2010/146581 A1 | 12/2010 |
| WO | 2011/013556 A1 | 2/2011 |
| WO | 2011/066961 A1 | 6/2011 |
| WO | 2011/082319 A1 | 7/2011 |
| WO | 2011/095352 A1 | 8/2011 |
| WO | 2011/106426 | 9/2011 |
| WO | 2011/110316 A1 | 9/2011 |
| WO | 2011135556 A1 | 11/2011 |
| WO | 2012/052982 A1 | 4/2012 |
| WO | 2012/064726 A1 | 5/2012 |
| WO | 2012/081020 A1 | 6/2012 |
| WO | 2012/120490 A2 | 9/2012 |
| WO | 2012/110619 A9 | 10/2012 |
| WO | 2012/156924 | 11/2012 |
| WO | 2013/016435 A1 | 1/2013 |
| WO | 2013/072777 A2 | 5/2013 |
| WO | 2013/105099 A2 | 7/2013 |
| WO | 2013/109756 A2 | 7/2013 |
| WO | 2013187927 A1 | 12/2013 |
| WO | 2014047650 A1 | 3/2014 |
| WO | 2014/081892 A1 | 5/2014 |
| WO | 2014/139845 A1 | 9/2014 |
| WO | 2014/169266 A1 | 10/2014 |
| WO | 2014/178198 A1 | 11/2014 |
| WO | 2015/061365 A1 | 4/2015 |
| WO | 2015103547 A1 | 7/2015 |
| WO | 2015/134625 A1 | 9/2015 |
| WO | 2015/179324 A2 | 11/2015 |
| WO | 2015/189354 | 12/2015 |
| WO | 2016/010995 A1 | 1/2016 |
| WO | 2016089451 A1 | 6/2016 |
| WO | 2017089424 A1 | 6/2017 |
| WO | WO 2017/161204 A1 | 9/2017 |
| WO | WO 2021/113302 A1 | 6/2021 |

OTHER PUBLICATIONS

Search Report issued in corresponding Chinese Patent Application No. 201680080064.4 dated Jun. 9, 2020 (English translation only).
U.S. Pat. No. 6,348,062, Jul. 8, 2003, Hopkins et al., Withdrawn.

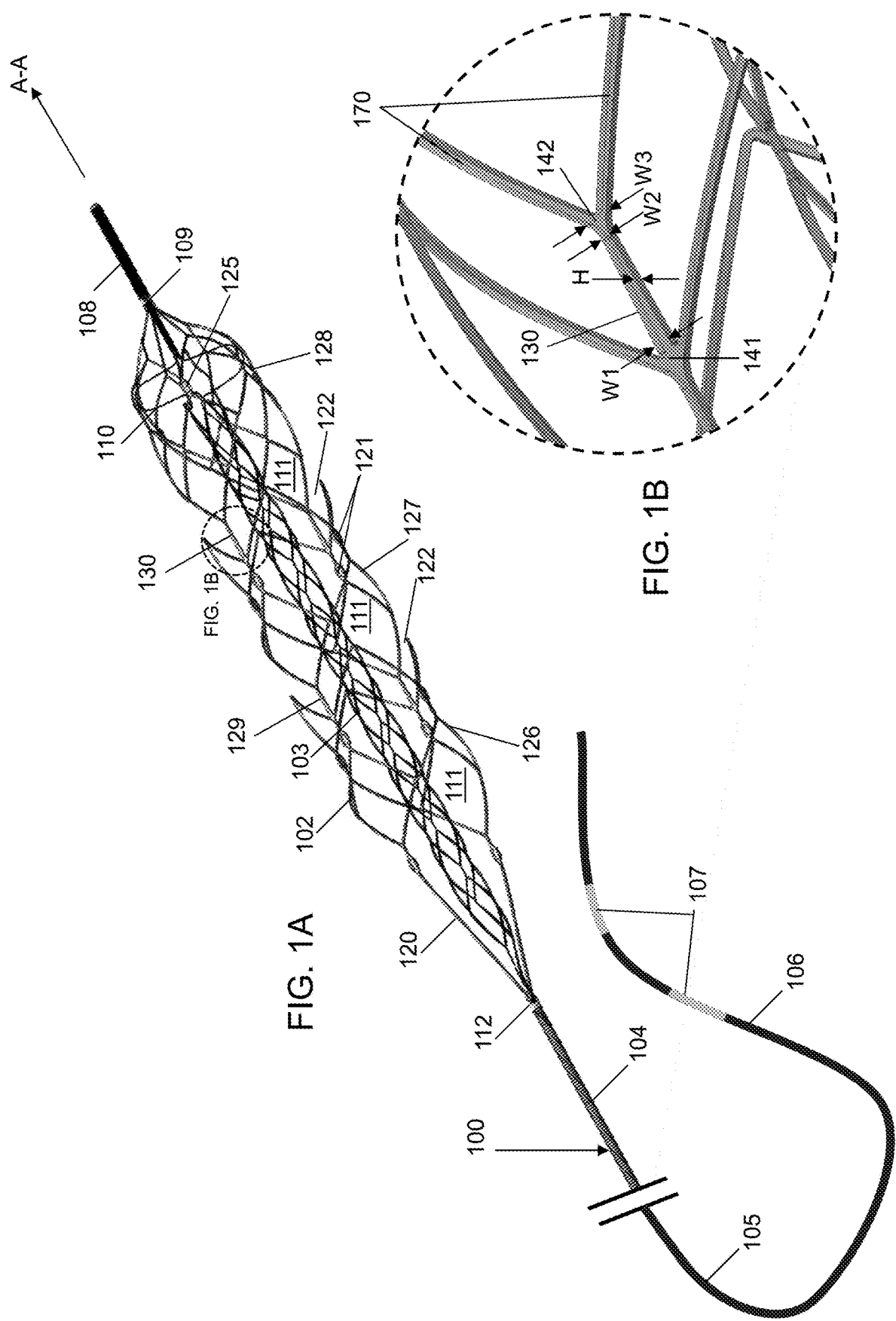

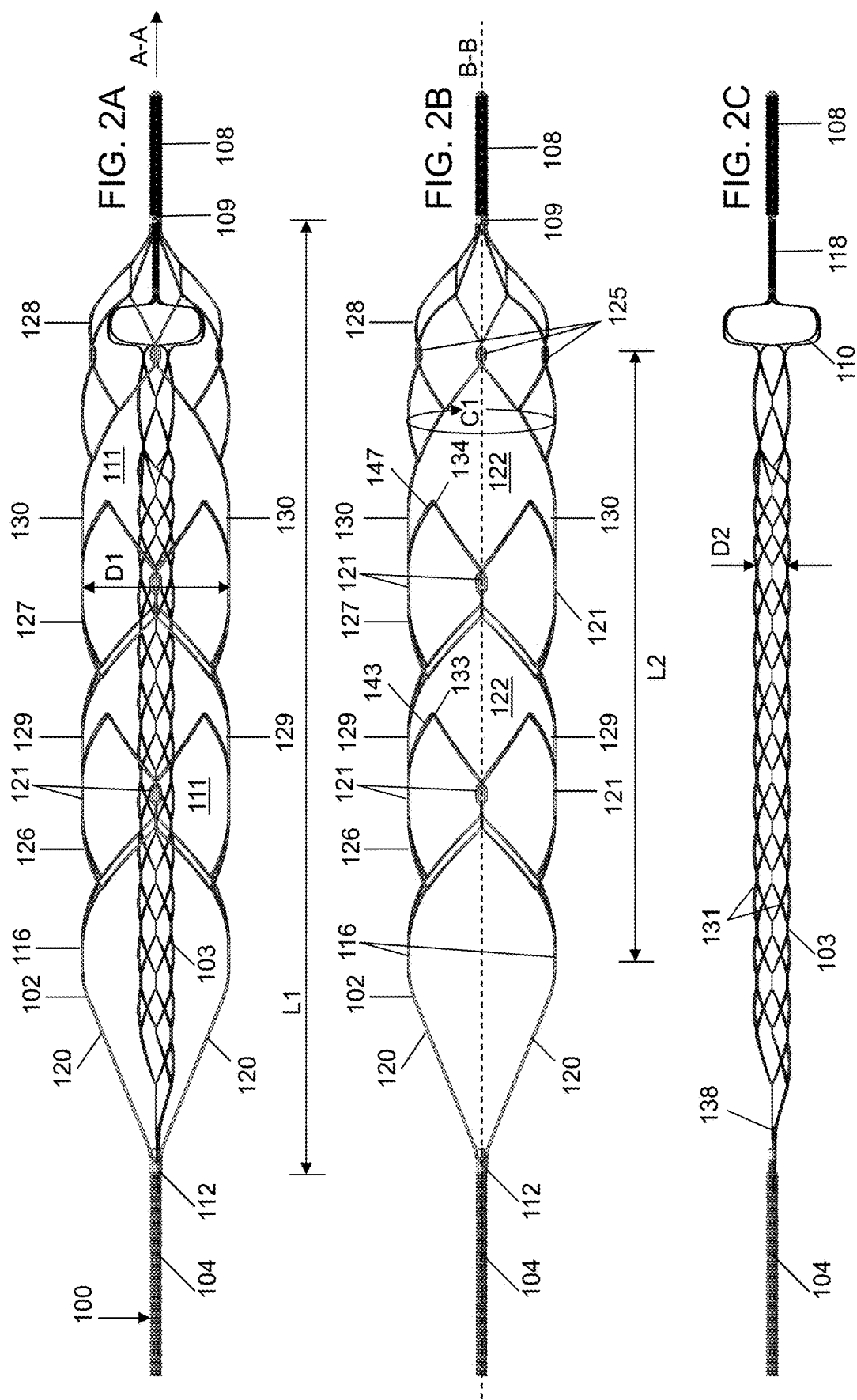

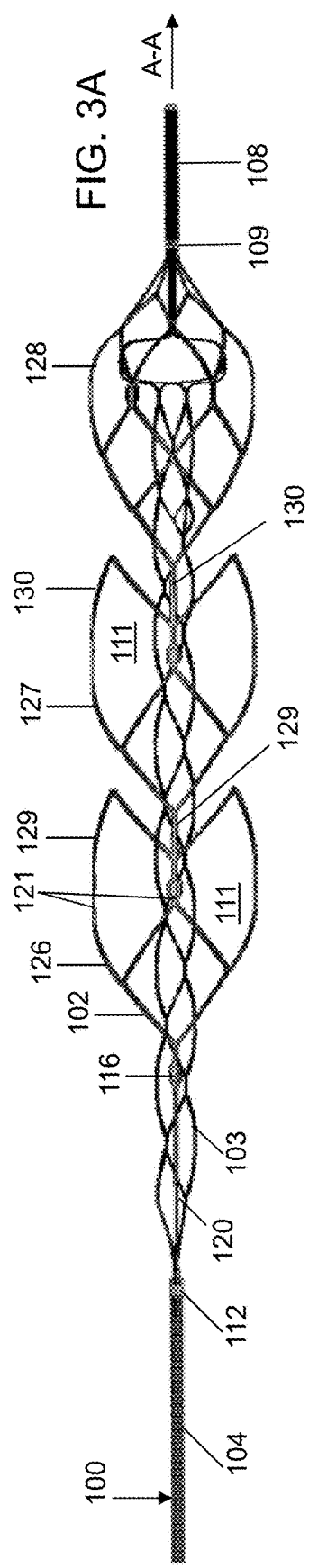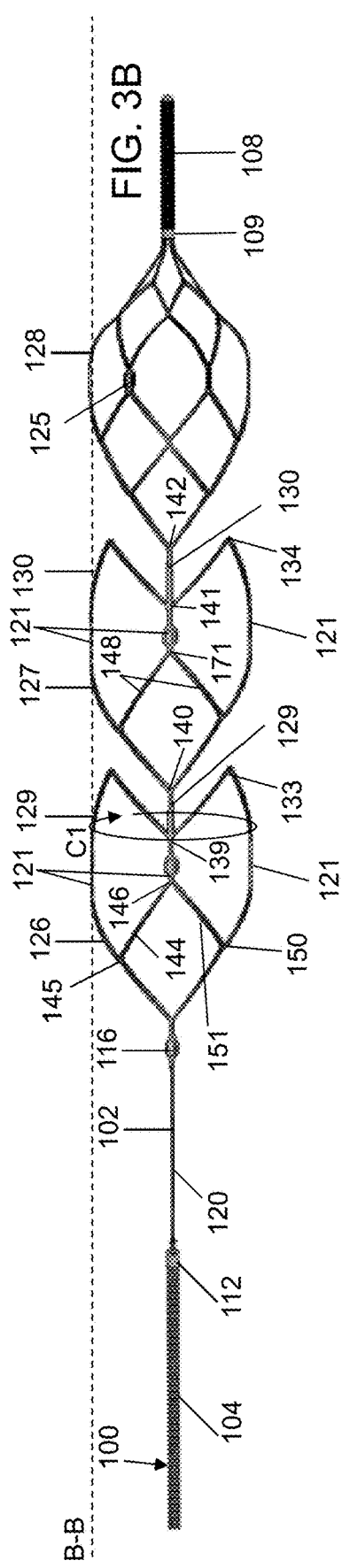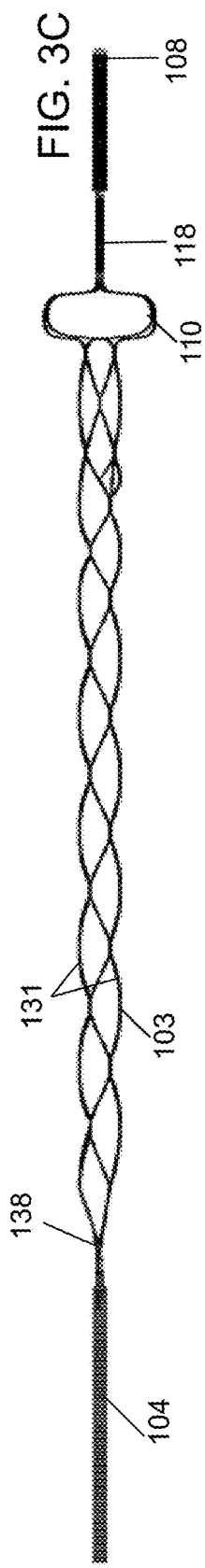

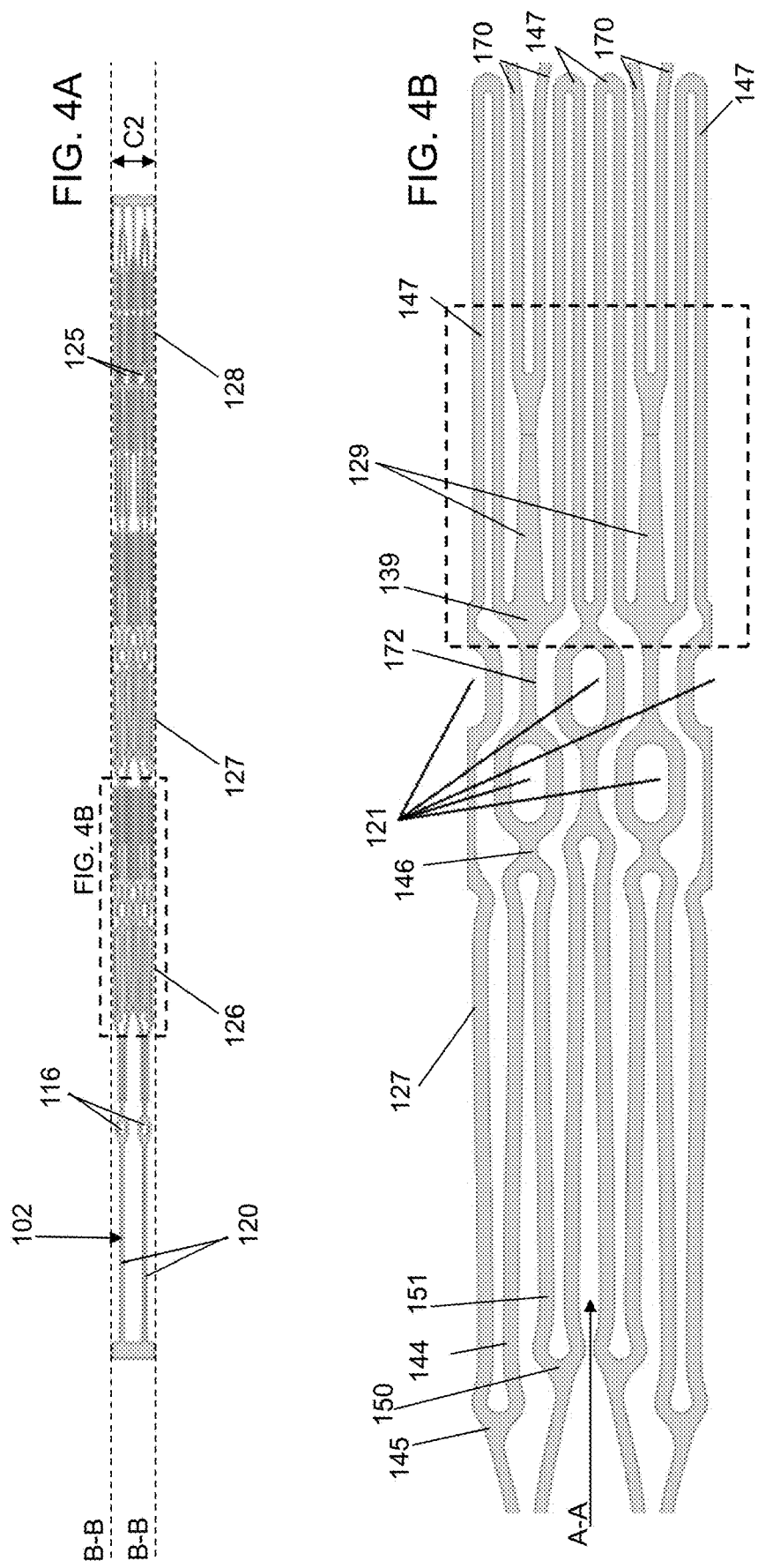

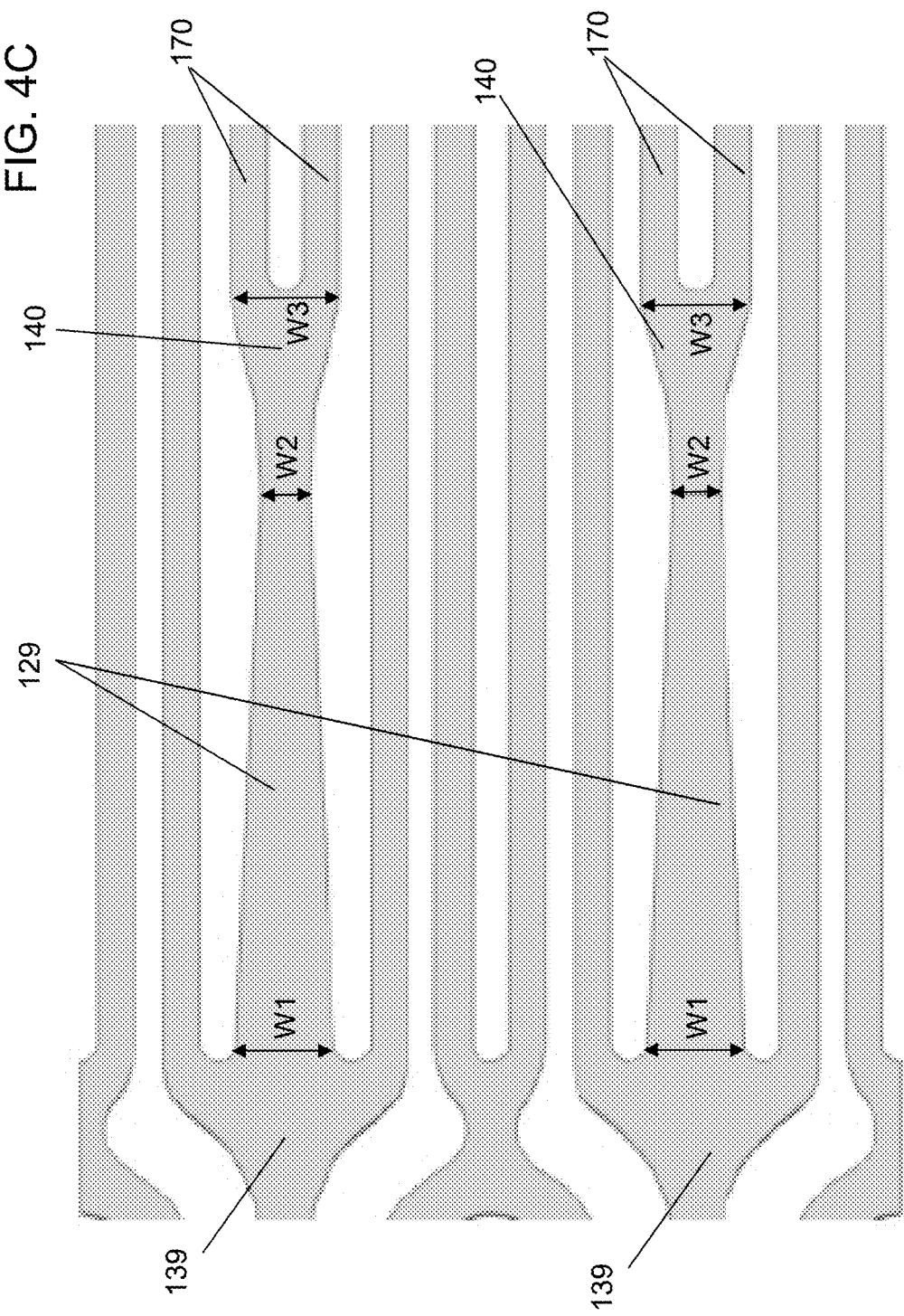

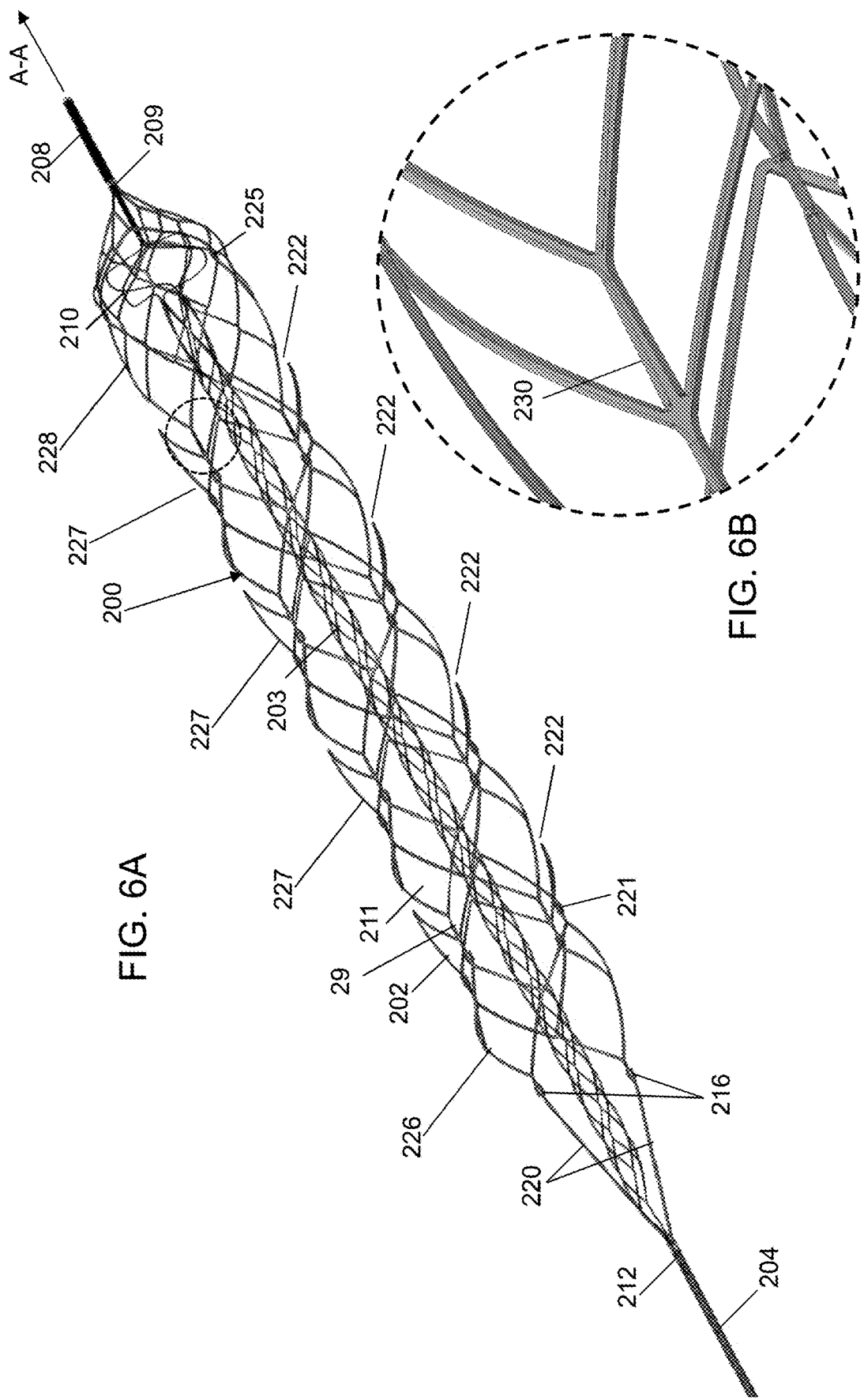

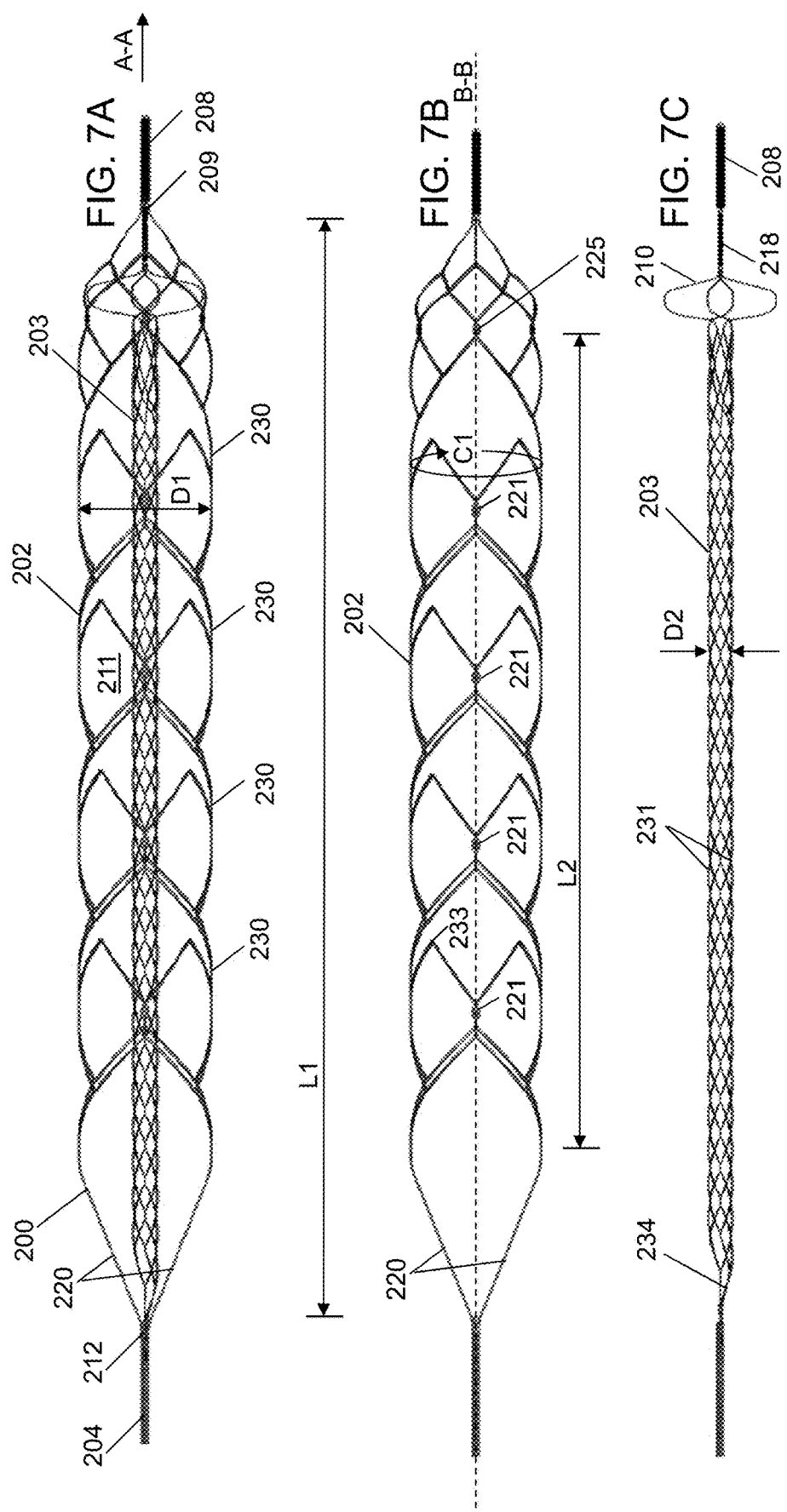

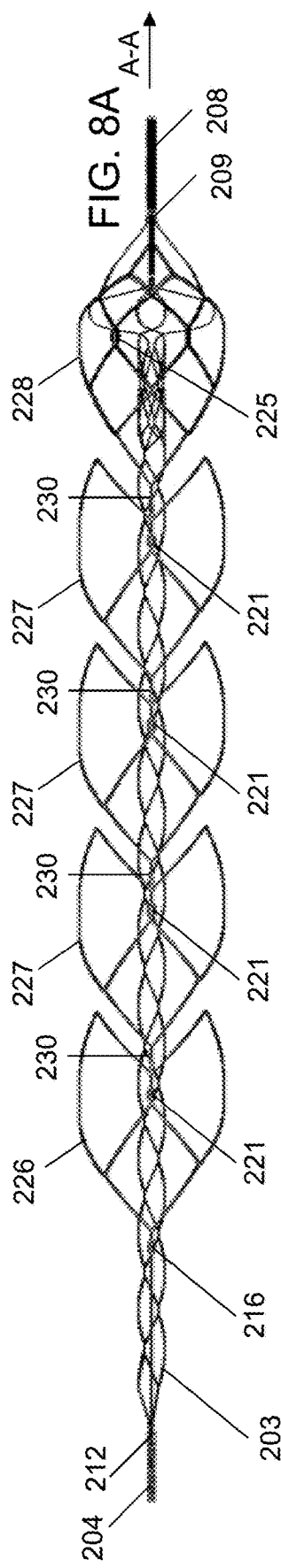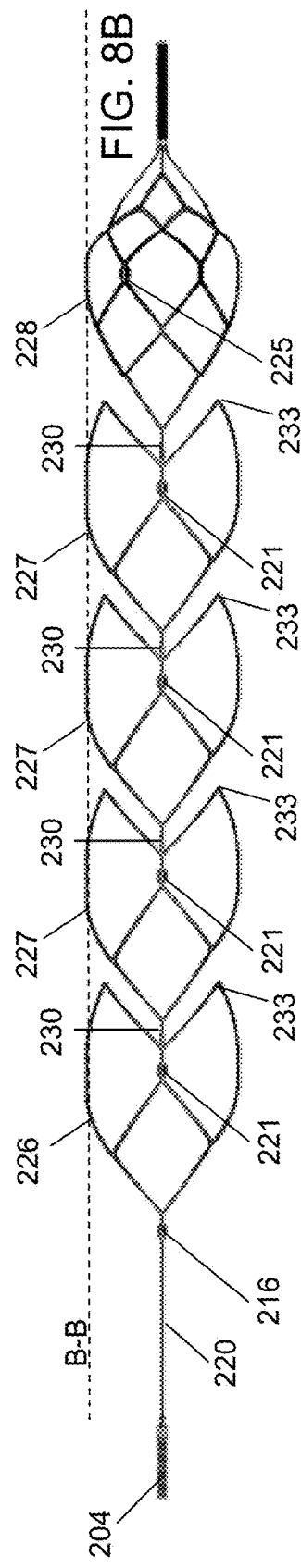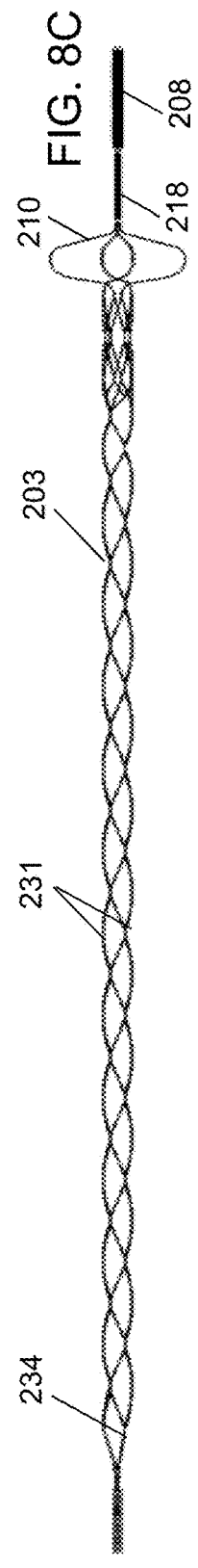

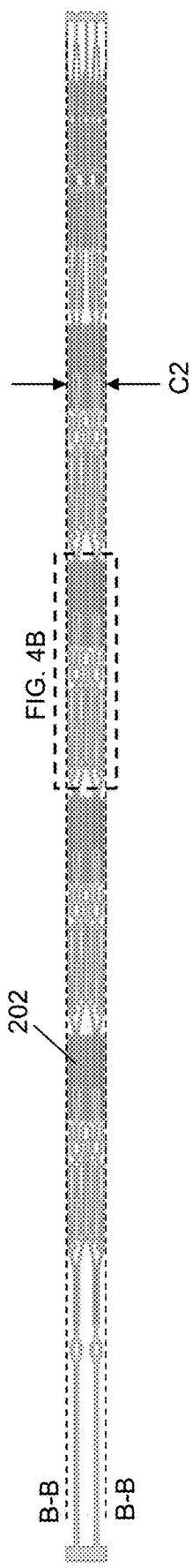

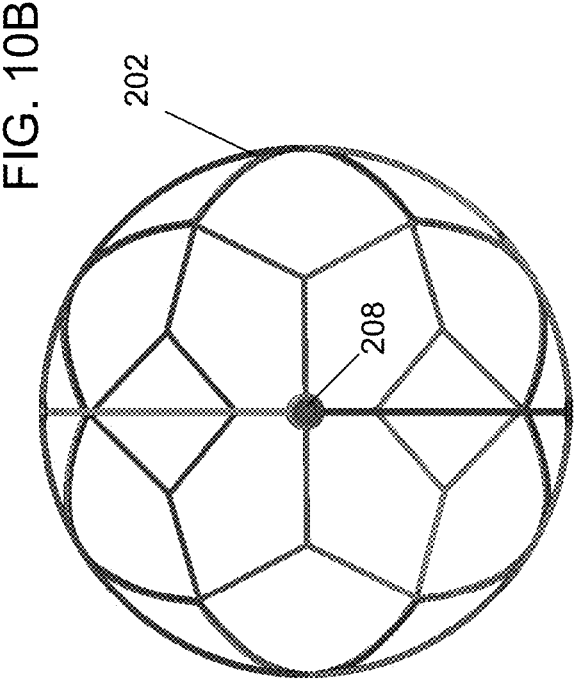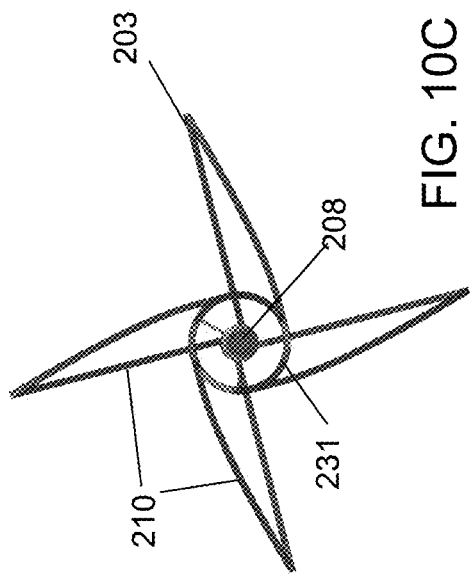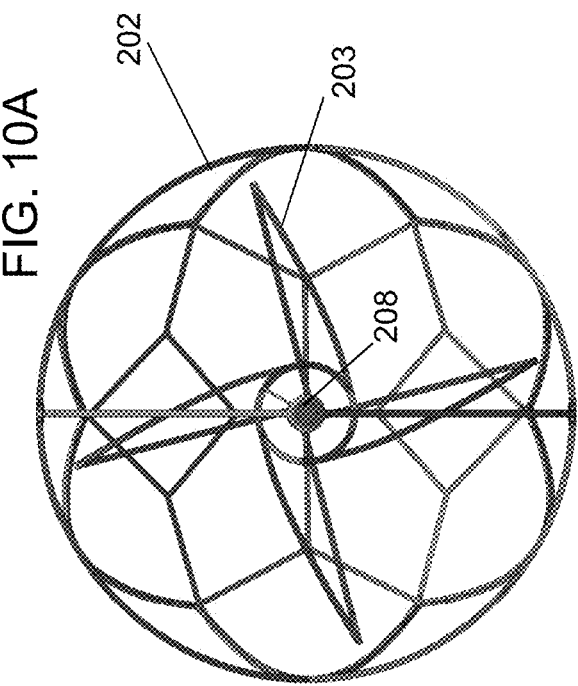

CLOT RETRIEVAL DEVICE WITH FLEXIBLE COLLAPSIBLE FRAME

FIELD OF THE INVENTION

This invention relates to devices and methods of removing acute blockages from blood vessels. More specifically, the invention relates to removing obstructions from cerebral arteries in patients suffering acute ischemic stroke (AIS), from pulmonary arteries in patients suffering from pulmonary embolism (PE), from coronary native or graft vessels in patients suffering from myocardial infarction (MI), and from other peripheral arterial and venous vessels in which a clot or other obstruction (e.g. misplaced device, migrated device, large emboli, etc.) is causing an occlusion.

BACKGROUND

Thromboembolism occurs when part or all of a thrombus breaks away from the blood vessel wall. This clot (now called an embolus) is then carried in the direction of blood flow. An ischemic stroke may result if the clot lodges in the cerebral vasculature. A pulmonary embolism may result if the clot originates in the venous system or in the right side of the heart and lodges in a pulmonary artery or branch thereof. Clots may also develop and block vessels locally without being released in the form of an embolus—this mechanism is common in the formation of coronary blockages.

There are a number of access challenges that make it difficult to deliver treatment devices to a clot or other obstruction. In cases where access involves navigating the aortic arch (such as coronary or cerebral blockages) the configuration of the arch in some patients makes it difficult to position a guide catheter. These difficult arch configurations are classified as either type 2 or type 3 aortic arches with type 3 arches presenting the most difficulty. The tortuosity challenge is even more severe in the arteries approaching the brain. For example, it is not unusual at the distal end of the internal carotid artery that the device will have to navigate a vessel segment with a 180° bend, a 90° bend and a 360° bend in quick succession over a few centimeters of vessel. In the case of pulmonary embolisms, access may be gained through the venous system and then through the right atrium and ventricle of the heart. The right ventricular outflow tract and pulmonary arteries are delicate vessels that can easily be damaged by inflexible or high profile devices. For these reasons it is desirable that an obstruction retrieval device be compatible with a delivery catheter having a low profile and high flexibility.

The vasculature in the area in which the clot may be lodged is often fragile and delicate. For example, neurovascular vessels are more fragile than similarly sized vessels in other parts of the body and are in a soft tissue bed. Excessive tensile forces applied on these vessels could result in perforations and hemorrhage. Pulmonary vessels are larger than those of the cerebral vasculature, but are also delicate in nature, particularly more superior vessels.

The clot may comprise any of a range of morphologies and consistencies. Long strands of softer clot material may tend to lodge at bifurcations or trifurcations, resulting in multiple vessels being simultaneously occluded over significant lengths. More mature and organized clot material is likely to be less compressible than softer fresher clot, and under the action of blood pressure it may distend the compliant vessel in which it is lodged.

The clots may not only range in shape and consistency, but also may vary greatly in length, even in any one given area of the anatomy. For example, clots occluding the middle cerebral artery of an ischemic stroke patient may range from just a few millimeters to several centimeters in length.

Stent-like clot retrievers are being increasingly used to remove clot and other obstructions from cerebral vessels of acute stroke patients. These are self-expanding devices, similar in appearance to a stent attached to the end of a long shaft and are advanced through a microcatheter and deployed across clot obstructions in order to trap and retrieve them. They rely on a pinning mechanism to grab the clot by trapping the clot between the self-expanding stent-like body and the vessel wall.

Typically, a stent-like clot retriever relies on its outward radial force (RF) to retain its grip on the clot. If the RF is too low the stent-like clot retriever will lose its grip on the clot, but if the RF is too high the stent-like clot retriever may damage the vessel wall and may require too much force to withdraw. Because clots vary in morphology across patients, RF required to grip the clot also varies. Because blood vessel fragility and geometry also varies across patients, RF required to reduce the risk of vessel trauma also varies.

In some treatments, some known stent-like clot retriever designs can lose their grip on a clot when withdrawn proximally around a bend in a tortuous vessel. This typically occurs because the struts of the stent-like clot retriever are placed in tension when it is retracted. This tension is due to friction between the device and the blood vessel and is increased if an additional load is applied load such as that provided by a clot. In a bend the struts on the outside of the bend are placed in higher tension than those on the inside. In order to attain the lowest possible energy state, the outside surface of the stent moves towards the inside surface of the bend, which reduces the tension in the struts, but also reduces the expanded diameter of the stent-like clot retriever.

Some treatments rely on pinning the clot between the stent-like clot retriever and the vessel wall and thus may not restrain the clot effectively when passing a branch vessel or when passing into a vessel that is larger than the fully expanded diameter of the stent-like clot retriever. Pinning the clot between the stent-like clot retriever and the vessel wall in order to remove it from the vessel also results in high shear forces against the side of the clot as it is removed, potentially releasing fragments of the clot. If these fragments are not retained by the device, they may be released leading to further blockages in the distal vasculature.

In some treatments, the stent-like clot retriever may be shorter than the clot itself. A device that is shorter than the clot is unlikely to be able to restore flow through the occluded area upon deployment, and thus the pressure gradient across the clot remains a significant impediment to its removal. Simply making such a device longer would likely render it difficult to track through tortuous anatomies and could be traumatic to the vasculature, taking more force to withdraw and potentially getting stuck and requiring surgery to remove.

For many reasons including some or all of the above limitations it is often necessary for a physician to make multiple passes with a clot retrieval device in order to fully remove an obstructive clot. However, each time a clot retrieval device is withdrawn the access to the target site is lost. The initial access steps of placing the large bore catheter do not need to be repeated as it remains in place after the initial clot retrieval attempt. Only the steps of accessing the clot site after the large bore catheter has been placed need to be repeated. Thus, it is necessary to re-advance a guidewire and microcatheter to access and re-cross the clot, and then remove the guidewire and advance the clot retrieval device through the microcatheter. Navigating the guidewire and microcatheter to the clot can take a considerable amount of time, especially if the vessels are tortuous. This additional time and device manipulation all adds to the risks to which the patient is exposed.

SUMMARY

Examples disclosed herein generally include a clot retrieval device having an inner expandable member and an outer expandable member, each formed from respective strut frameworks such that the outer expandable member has larger cell openings than the inner expandable member. The outer expandable member can have multiple discontinuous body segments spaced apart in relation to a longitudinal axis of the device. Adjacent discontinuous body segments can be joined by a pair of tapered connecting arms that are able to bend with a small radius of curvature compared to the body segments. This small radius of curvature can have a range of values depending on the tortuosity of the vasculature the device is expanded in. It will approximately equal 0 mm when the device is in a straight vessel and will approximately equal 0.5 mm when the device is in a vessel with a 180-degree bend. Some or all of the body segments can include radiopaque markers positioned to illustrate a circumference of the respective body segment and slightly staggered in relation to a longitudinal axis of the device such that the markers nest when the device is collapsed for delivery.

An example clot retrieval device has a collapsed configuration and an expanded configuration. The clot retrieval device is configured to remove clot from a blood vessel. The clot retrieval device has an inner expandable member and an outer expandable member. The inner expandable member has a first framework of struts and the outer expandable member has a second framework of struts. The second framework at least partially radially surrounds the inner expandable member.

Closed cells of the second framework of the outer expandable member can be larger than closed cells of the first framework of the inner expandable member.

The outer expandable member can have a first and a second body segment connected by two connecting arms, wherein the first body segment is positioned in a proximal direction in relation the second body segment. Each of the two connecting arms respectively can have a tapered shape that is wider where the arm is near the first, proximal body segment and narrower where the arm is near the second, distal body segment. As shown in FIG. 1B and FIG. 4C, approximate values for the labelled dimensions are as follows; the height 'H' has a value of 0.075 mm, the strut width 'W1' has a value of 0.16 mm, the strut width 'W2' has a value of 0.08 mm and the strut width 'W3' has a value of 0.20 mm. Hence, the approximate percentage change in width between 'W1' and 'W2' is a decrease of 50% and the approximate percentage change in width between 'W2' and 'W3' is an increase of 60%. The outer expandable member can have additional body segments connected to the first and/or second body segment by additional connecting arms.

The outer expandable member can have at least two inlet mouths in the second framework including a pair of inlet mouths between the first and second body segments. Each of the two inlet mouths between the first and second body segment can have a respective opening bounded by the first body segment, the second body segment, and the two connecting arms.

The first body segment can have at least two pairs of struts each terminating in a respective distal apex and forming a proximal boundary of a respective inlet mouth of the two inlet mouths.

The two connecting arms between the first and second body segments of the outer expandable member can extend substantially parallel to a longitudinal axis of the device.

The two connecting arms between the first and second body segments of the outer expandable member can be positioned approximately 180° from each other about a circumference of the outer expandable member.

The first body segment and the second body segment can be connected to each other solely via the two connecting arms.

Each of the two connecting arms can be configured to bend with a curvature having a radius smaller than a radius of curvature of a majority of struts of the first body segment and the second body segment as the clot retrieval device is pulled proximally through a tubular vasculature comprising a bend of about 180°.

The outer expandable member can have three or more body segments each shaped substantially similarly to the first body segment and the second body segment. The outer expandable member can include pairs of tapered connecting arms such that each respective pair of tapered connecting arms joins longitudinally adjacent body segments of the three or more body segments. The tapered connecting arms can be shaped and oriented similarly to the connecting arms between the first and second body segments.

One or both of the first and second body segments can respectively include four or more radiopaque markers positioned around a circumference of the respective body segment. When the clot retrieval device is in the collapsed configuration, each of the radiopaque markers can be offset from adjacent radiopaque markers of the four or more radiopaque markers. The markers can be offset from adjacent radiopaque makers in relation to a longitudinal axis of the device. When the clot retrieval device is in the collapsed configuration, alternating radiopaque markers of the four or more radiopaque markers can be aligned in a plane orthogonal to the longitudinal axis.

The first body segment can include a first set of four or more radiopaque markers. The second body segment can include a second set of four or more radiopaque markers. When the clot retrieval device is in the expanded configuration, the first and second sets of four or more radiopaque markers are spaced approximately 8 millimeters apart, measured in the direction of the longitudinal axis. When the clot retrieval device is in the collapsed configuration, the first and second sets of four or more radiopaque markers are spaced approximately 10 millimeters apart, measured in the direction of the longitudinal axis.

Each of the four or more radiopaque markers can include radiopaque material positioned in an eyelet.

At least two of the four or more radiopaque markers can be aligned, in the direction of the longitudinal axis, with a respective connecting arm of the two connecting arms.

Another example clot retrieval device can have a collapsed configuration and an expanded configuration. The clot retrieval device is configured to remove clot from a blood vessel. Structures and functionality of this example clot retrieval device are combinable with structures and features of the previous example clot retrieval device.

The example clot retrieval device includes an inner expandable member having a first framework of struts and an outer expandable member having a second framework of struts. The second framework of struts can form closed cells larger than closed cells of the first framework of inner expandable member. The second framework can at least partially radially surround the first framework of the inner expandable member.

The example clot retrieval device can include four or more radiopaque markers affixed to the second framework of struts and positioned to indicate a circumference of the outer expandable member. The radiopaque markers can be further positioned such that when the clot retrieval device is in the collapsed configuration, each of the radiopaque markers is offset, in relation to a longitudinal axis of the device to respective circumferentially adjacent radiopaque markers.

The outer expandable member can include discontinuous body segments spaced apart from each other in the direction of the longitudinal axis. The radiopaque markers can be positioned to indicate a circumference of a body segment of the discontinuous body segments.

The example clot retrieval device can include a first body segment and a second body segment, wherein the first body segment is positioned in a proximal direction in relation the second body segment. The outer expandable member can include two connecting arms joining the first body segment to the second body segment. Each of the two connecting arms can respectively have a tapered shape that is wider near the proximal, first body segment and narrower near the distal, second body segment.

At least two of the four or more radiopaque markers can be aligned, in the direction of the longitudinal axis, with a respective connecting arm of the two connecting arms.

The outer expandable member can include two inlet mouths in the second framework. Each of the two inlet mouths can include a respective opening bounded by the first body segment, the second body segment, and the two connecting arms.

The first body segment can include the four or more radiopaque markers forming a first set of markers, and the second body segment can include a second set of four or more radiopaque markers positioned to indicate a circumference of the second body segment. The second set of radiopaque markers can be positioned such that when the clot retrieval device is in the collapsed configuration, each of the radiopaque markers of the second set is offset, in relation to a longitudinal axis of the device to respective adjacent radiopaque markers of the second set. Markers in the first set of radiopaque markers can be similarly offset.

The two connecting arms can be positioned approximately 180° from each other about a circumference of the outer expandable member.

BRIEF DESCRIPTION OF THE DRAWINGS

FIG. 1A shows an isometric view of an example clot retrieval device according to aspects of the present invention.

FIG. 1B shows a close-up of a portion of the clot retrieval device illustrated in FIG. 1A, the portion including a tapered strut according to aspects of the present invention.

FIG. 2A shows a plan view of a first side of the clot retrieval device illustrated in FIG. 1A.

FIG. 2B shows the view clot retrieval device as illustrated in FIG. 2A having an inner expandable member of the clot retrieval device removed from the illustration.

FIG. 2C shows the view of the clot retrieval device as illustrated in FIG. 2A having an outer expandable member of the clot retrieval device removed from the illustration.

FIG. 3A shows a plan view of a second side of the clot retrieval device illustrated in FIG. 1A, the second side viewed at 90° from the first side view illustrated in FIG. 2A.

FIG. 3B shows the view clot retrieval device as illustrated in FIG. 3A having the inner expandable member of the clot retrieval device removed from the illustration.

FIG. 3C shows the view of the clot retrieval device as illustrated in FIG. 3A having the outer expandable member of the clot retrieval device removed from the illustration.

FIG. 4A shows a linear view of the outer expandable member of the clot retrieval device cut along a centerline indicated in FIGS. 2B and 3B and flattened.

FIG. 4B shows a close-up of a portion of the outer expandable member of the clot retrieval device as indicated in FIG. 4A.

FIG. 4C shows a close-up of a portion of the outer expandable member of the clot retrieval device as indicated in FIG. 4B.

FIG. 6A shows an isometric view of another example clot retrieval device according to aspects of the present invention.

FIG. 6B shows a close-up of a portion of the clot retrieval device illustrated in FIG. 6A, the portion including a tapered strut according to aspects of the present invention.

FIG. 7A shows a plan view of a first side of the clot retrieval device illustrated in FIG. 6A.

FIG. 7B shows the view clot retrieval device as illustrated in FIG. 7A having an inner expandable member of the clot retrieval device removed from the illustration.

FIG. 7C shows the view of the clot retrieval device as illustrated in FIG. 7A having an outer expandable member of the clot retrieval device removed from the illustration.

FIG. 8A shows a plan view of a second side of the clot retrieval device illustrated in FIG. 6A, the second side viewed at 90° from the first side view illustrated in FIG. 7A.

FIG. 8B shows the view clot retrieval device as illustrated in FIG. 8A having the inner expandable member of the clot retrieval device removed from the illustration.

FIG. 8C shows the view of the clot retrieval device as illustrated in FIG. 8A having the outer expandable member of the clot retrieval device removed from the illustration.

FIG. 9 shows a linear view of the outer expandable member of the clot retrieval device cut along a centerline indicated in FIGS. 7B and 8B and flattened.

FIG. 10A shows a plan view of a distal end of the clot retrieval device illustrated in FIG. 6A.

FIG. 10B shows the view clot retrieval device as illustrated in FIG. 10A having the inner expandable member of the clot retrieval device removed from the illustration.

FIG. 10C shows the view of the clot retrieval device as illustrated in FIG. 10A having the outer expandable member of the clot retrieval device removed from the illustration.

DETAILED DESCRIPTION

Figure 5B:
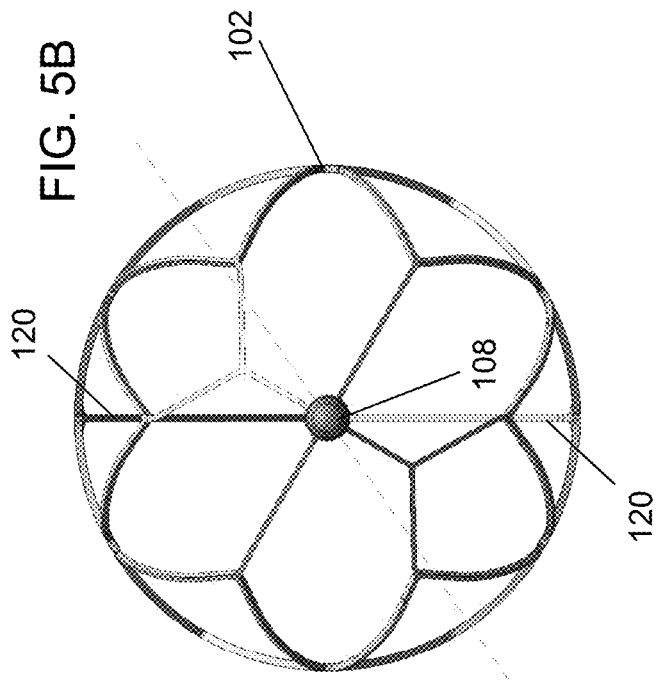
FIG. 5B shows the view clot retrieval device as illustrated in FIG. 5A having the inner expandable member of the clot retrieval device removed from the illustration.

Specific embodiments of the present invention are now described in detail with reference to the figures, wherein identical reference numbers indicate identical or functionality similar elements. The terms "distal" or "proximal" are used in the following description with respect to a position or direction relative to the treating physician. "Distal" or "distally" are a position distant from or in a direction away from the physician. "Proximal" or "proximally" or "proximate" are a position near or in a direction toward the physician.

Accessing cerebral, coronary and pulmonary vessels involves the use of a number of commercially available products and conventional procedural steps. Access products such as guidewires, guide catheters, angiographic catheters and microcatheters are described elsewhere and are regularly used in catheter lab procedures. It is assumed in the descriptions below that these products and methods are employed in conjunction with the device and methods of this invention and do not need to be described in detail.

The following detailed description is merely exemplary in nature and is not intended to limit the invention or the application and uses of the invention. Although the description of the invention is in many cases in the context of treatment of intracranial arteries, the invention may also be used in other body passageways as previously described.

FIG. 1A shows a distal portion of an example clot retrieval device 100 in an expanded configuration. The clot retrieval device 100 generally extends to define a longitudinal axis A-A and has a distal coil 108 at its distal end, an outer expandable member 102 and an inner expandable member 103 extending proximally and coaxially from the distal coil 108, and a proximal coil 104 extending proximally from the outer expandable member 102 and the inner expandable member 103. The device 100 can include additional features such as an elongate shaft 106, a sleeve 105, and indicator bands 107. The device 100 can include a distal junction or collar 109 joining the distal coil 108 to the outer expandable member 102 and the inner expandable member 103. The device 100 can include a proximal junction or collar 112 joining the proximal coil 104 to the outer expandable member 102 and the inner expandable member 103. The junctions 109, 112 can be constructed as usable with a clot retrieval device having two expandable layers 102, 103 such as described in U.S. Pat. No. 10,390,850 incorporated herein by reference as if set forth herein in its entirety.

FIG. 1B shows a close-up of a portion of the clot retrieval device illustrated in FIG. 1A, the portion including a tapered strut according to aspects of the present invention.

Figure 5C:
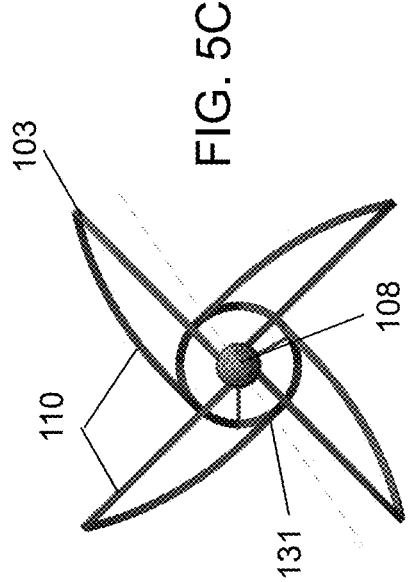
FIG. 5C shows the view of the clot retrieval device as illustrated in FIG. 5A having the outer expandable member of the clot retrieval device removed from the illustration.
Figure 5A:
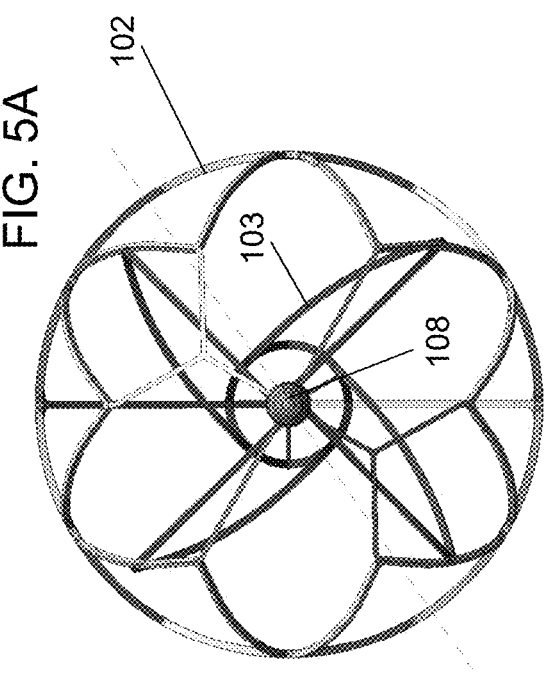
FIG. 5A shows a plan view of a distal end of the clot retrieval device illustrated in FIG. 1A.

FIG. 2A shows a plan view of a first side of the clot retrieval device 100. FIG. 2B shows the view clot retrieval device 100 as illustrated in FIG. 2A having the inner expandable member 103 removed for the purpose of illustration. FIG. 2C shows the view of the clot retrieval device 100 as illustrated in FIG. 2A having the outer expandable member 102 removed for the purpose of illustration. FIG. 3A shows a plan view of a second side of the clot retrieval device 100, the second side viewed at 90° from the first side view illustrated in FIG. 2A. FIG. 3B shows the view clot retrieval device 100 as illustrated in FIG. 3A having the inner expandable member 103 removed for the purpose of illustration. FIG. 3C shows the view of the clot retrieval device 100 as illustrated in FIG. 3A having the outer expandable member 102 removed for the purpose of illustration. FIG. 4A shows a linear view of the outer expandable member 102 cut along a line B-B indicated in FIGS. 2B and 3B and flattened. FIG. 4B shows a close-up of a portion of the outer expandable member 102 as indicated in FIG. 4A. FIG. 4C shows a close-up of a portion of the outer expandable member 102 as indicated in FIG. 4B. FIG. 5A shows a plan view of a distal end of the clot retrieval device 100. FIG. 5B shows the view of the clot retrieval device 100 as illustrated in FIG. 5A having the inner expandable member 103 removed for the purpose of illustration. FIG. 5C shows the view of the clot retrieval device 100 as illustrated in FIG. 5A having the outer expandable member 102 removed for the purpose of illustration.

As described in greater detail in relation to FIGS. 1B and 4C, the outer expandable member 102 can include tapered struts 129, 130 joining body segments 126, 127, 128. The tapered struts 129, 130 are shaped to provide flexibility to the outer expandable member 102 to facilitate withdraw of the device 100 from tortuous vascular when an obstruction is at least partially confined by the outer expandable member 102. Additionally, or alternatively, the tapered struts 129, 130 are shaped to promote apposition of the outer expandable member 102 circumferentially to blood vessel walls as the device 100 is withdrawn through tortuous vasculature when an obstruction is at least partially confined by the outer expandable member 102.

As described in greater detail in relation to FIGS. 4A and 4B, the outer expandable member 103 can include staggered radiopaque markers positioned to facilitate visualization of the device 100 during treatment while also maintaining a small profile collapsed configuration of the outer expandable member 102 to facilitate traverse of the collapsed device 100 across a clot or other obstruction.

Referring collectively to FIGS. 1A through 5C, the outer expandable member 102 and inner expandable member 103 are collapsible into a restraining sheath (e.g. microcatheter) sized to traverse a clot or other obstruction. The outer expandable member 102 and inner expandable member 103 are each configured to self-expand upon release from the restraining sheath. In the expanded configuration, the device 100 can facilitate clot retrieval, flow restoration, and/or fragmentation protection.

Both the inner and outer expandable members 102, 103 are preferably made from a material capable of recovering its shape automatically once released from a constricted delivery configuration. A super-elastic or pseudo-elastic material such as Nitinol or an alloy of similar properties is particularly suitable. The material can have a high recoverable strain sufficient to resiliently collapse and expand as described herein. The material could be in many forms such as wire or strip or sheet or tube. A particularly suitable manufacturing process is to laser cut a Nitinol tube and then heat set and electropolish the resultant structure to create a framework of struts and connecting elements. This framework can be any of a huge range of shapes as understood by a person skilled in the pertinent art according to the teachings disclosed herein. The framework may be rendered visible under fluoroscopy through the addition of alloying elements or through a variety of other coatings or marker bands. For instance, the framework can include material and/or markers with radiopaque material including, but not limited to Barium Sulphate, Bismuth SubCarbonate, Barium OxyChloride, Gold, Tungsten, Platinum, Iridium, Tantalum, and alloys thereof. Specifically, in some examples, the framework can include radiopaque markers having an Iridium alloy, and more specifically a Platinum-Iridium alloy.

The inner expandable member 103 is preferably configured to expand to a lesser diameter D2 than that of the smallest vessel in which it is intended to be used. This diameter D2 is typically less than 50% that of the diameter D1 of the outer expandable member 102 and may be as low as 20% or less of the outer member diameter D1.

A distal scaffolding zone can incorporate strut elements from the framework of the outer and/or inner expandable members 102, 103 such as an expanded portion 110 of the inner expandable member 103 and a distal portion 128 of the outer expandable member 102. The strut geometry of the distal scaffolding zone can be shaped as illustrated herein, or as described in relation to compatible stent-like clot retrievers, including but not limited to as disclosed in U.S. Pat. No. 10,390,850. The distal scaffolding zone can further include fine wires or fibers to provide added scaffolding with minimal impact of overall device profile or deliverability. Suitable materials ideally have a high tensile strength so that a very fine wire or fiber with sufficient integrity for manufacturability and use can be produced, such as for example polymers materials like UHMWPE, Aramid, LCP, PET or PEN, or metals such as Tungsten, MP35N, stainless steel or Nitinol.

In each of the expanded configuration and the collapsed configuration, the inner expandable member 103 and outer expandable members define respective tubular bodies. Preferably the tubular bodies are coaxial about the longitudinal axis A-A. The device 100 includes a reception space 111 within the outer expandable member 102 and outside the inner expandable member 103 when the inner and out expandable members 102, 103 are in the expanded configuration. The device 100 and reception space 111 are sized, shaped, and otherwise configured to allow a clot to become at least partially confined within the reception space during a clot removal treatment. The interior of the inner expandable member 103 when expanded is configured to provide a flow path through which blood can flow when the device 100 is expanded through a clot.

During a clot removal treatment, the length of the outer expandable member 102 can be about as long as the length of the occlusive clot or longer to remove many of the degrees of freedom of movement freedom otherwise available to the clot. The outer member 102 includes inlet openings 222 sized, shaped, another otherwise configured to provide the primary freedom of movement available to the clot and so the expansion of the outer member 102 urges the clot into the reception space 111. The outer member 102 has multiple inlet mouths 122 to accept the clot. In this way inlet mouths 122 allow portions of the clot to enter reception space 111 of the outer member 102, and thus allow the clot to be retrieved without being excessively compressed. This is advantageous because the inventors have discovered that compression of clot causes it to dehydrate, which in turn increases the frictional properties of the clot, and increases its stiffness, all of which makes the clot more difficult to disengage and remove from the vessel. This compression can be avoided if the clot migrates inward through the scaffolding of the outer member 102 as the scaffolding migrates outward towards the vessel wall.

The inlet mouths 122 can further allow the outer member 102, when retracted, to apply a force to the clot in a direction substantially parallel to the direction in which the clot is to be pulled from the vessel (i.e. substantially parallel to the central axis of the vessel). This means that the outward radial force applied to the vasculature may be kept to a minimum, which in turn means that the action of the clot retrieval device 100 on the clot does not serve to increase the force required to dislodge the clot from the vessel, thus protecting delicate cerebral vessels from harmful radial and tensile forces.

The outer expandable member 102 includes proximal struts 120 connected at their proximal ends to the proximal collar 112 and at their distal ends to a proximal body segment 126. The proximal struts 120 can have a tapered profile or be otherwise configured to provide a gradual stiffness transition from the shaft 106 to the tubular body of the outer expandable member 102.

The proximal body segment 126 is connected to a middle body segment 127 by two connecting arms 129, which run from a proximal junction 139 to a distal junction 140. The middle body segment 127 is in turn connected to a distal body segment 128 by two connecting arms 130, which run from a proximal junction 141 to a distal junction 142. The region between the middle and distal body segments 127, 128 includes two inlet mouths 122 through which clot may pass and enter the reception space 111 defined by the region between the inner and outer members 102, 103.

As illustrated in greater detail in FIGS. 1B and 4C, each of the connecting arms 129 can have a tapered profile with a width that tapers from a wider dimension W1 at the respective proximal junction 139, 141 to a narrower width W2 near the respective distal junction 140, 142. At the distal junction 140, 142, the connecting arms 129, 130 can expand to a width W3 that is wider than the narrower width W2 to accommodate branching distal struts 170. The connecting arms 129, 130 can have a height H (thickness) that is substantially uniform. The height H can be consistent with the strut thickness of the majority of the outer expandable member 102.

In one example, as shown in FIG. 1B and FIG. 4C, approximate values for the labelled dimensions are as follows; the height H has a value of about 0.075 mm, the proximal strut width W1 has a value of about 0.16 mm, the distal strut width W2 has a value of about 0.08 mm and the bifurcation strut width W3 has a value of about 0.20 mm. Hence, the approximate percentage change in width between the proximal width W1 and the distal width W2 is a decrease of 50% and the approximate percentage change in width between the distal width W2 and the bifurcation width W3 is an increase of 60%.

Figure 11B:
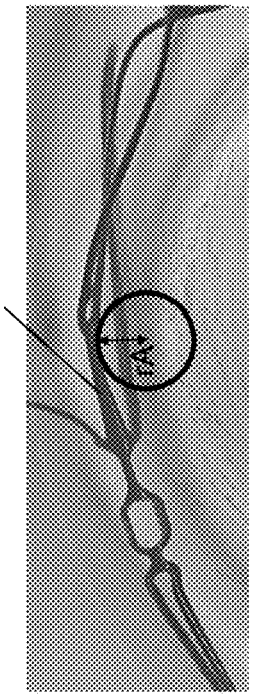
FIG. 11B shows a close-up of a portion of the outer expandable member as indicated in FIG. 11A.

The tapered shape of the connecting arms 129, 130 can be configured to bend to reduce withdrawal force around blood vessel bends compared to a similarly constructed stent-like clot retriever device having non-tapered connecting arms. The arms 129, 130 can be configured to bend with a curvature having a larger curvature (smaller radius of curvature) compared to a majority of struts within the outer expandable member 102. (See radius r as illustrated in FIG. 11B.)

The connecting arms 129 between the proximal body segment 126 and the middle body segment 127 of the outer expandable member 102 can be substantially aligned with the connecting arms 130 between the middle and distal body segments 127, 128 to align the neutral axis of the body segments 126, 127, 128 during bending. In another embodiment the connecting arms 129 between the proximal body segment 126 and the middle body segment 127 can be aligned at an angle, such as 90° to the connecting arms 130 between the middle and distal body segments 127, 128.

As illustrated in greater detail in FIGS. 2B and 3B, the proximal body segment 126 includes interconnected struts, with certain struts such as strut 143 terminating in a distal apex 133 with no distal connecting elements, and other struts such as 144 terminating in junction points 145, 146. The middle body segment 127 includes interconnected struts, with certain struts such as strut 147 terminating in a distal apex 134 with no distal connecting elements, and other struts such as strut 148 terminating in junction points 171.

One or more of the body segments 126, 127, 128 can include marker bands or radiopaque features such as gold or platinum marker or coils. In the illustrated embodiment, oval markers 121, 125 are shown fixed in eyelets on struts on the proximal, middle, and distal body segments 126, 127, 128. The markers 125 on the distal body segment 128 can be positioned to indicate to the user the position of the distal body segment 128 and therefore distal portion of the device 100 to aid in accuracy of deployment of the device 100. The distal body segment 128 can include a single marker 125 to indicate the position of the distal body segment 128, or multiple markers to indicate a circumference of the distal body segment 128. Each of the proximal and middle body segments 126, 127 can include multiple oval markers 121 positioned circumferentially around the respective body segment 126, 127 to indicate to the user the expanded circumference C1 and/or position of the respective body segments 126, 127 during a treatment (where the circumference C1 is the diameter D1 times pi). In the illustrated embodiment, each of the proximal and middle body segments 126, 127 includes four markers 121 positioned approximately equidistant around a circumference C1 of the outer expandable member 102.

FIGS. 4A and 4B illustrate the outer expandable member 102 cut along the line B-B as indicated in FIGS. 2B and 3B, laid flat, and collapsed so to a height C2 corresponding to a circumference of the outer expandable member 102 when the device 100 is constrained by a microcatheter or sheath. As illustrated in greater detail in FIG. 4B, the markers 121 on each of the proximal body segment 126 and the middle body segment 127 are staggered, offset in the direction of the longitudinal axis A-A (i.e. positioned at different distances from the proximal collar 112) to facilitate collapse of the height C (circumference) of the outer expandable member 102. Each of the respective markers 121 connect to an elongated segment 172 which is shaped to nest the adjacent markers 121 between a junction (e.g. junction 141) and the respective connected marker 121. The elongated segments 172 and markers 121 are positioned in an alternating fashion circumferentially.

The struts in the body segments 126, 127, 128 can be configured so that during loading, crowns or junctions (e.g. junction 145 and junction 150 and other similarly shaped junctions) do not align at the same distance from the proximal collar. During loading or re-sheathing, a higher force is generally required to load a junction (crown) than a strut into the sheath, therefore if multiple crowns are loaded at the same time the user may notice an increase in loading force. By offsetting the crowns by making alternative struts 144 and 151 different lengths the loading force may be reduced and the perception to the user is improved.

The distal end of the distal body segment 128 includes struts forming a tapered shape terminating at the distal junction point 109, thus defining a closed end distal to the outer member 102. The distal body segment 128 is viewed from the distal end of the device 100 in a planar view in FIG. 5A with the inner expandable member 103 removed in FIG. 5B for the purposes of illustration and the outer expandable member 102 removed in FIG. 5C for the purposes of illustration. The distal end of the distal body segment 128 can include a distal framework as illustrated herein, or an alternative distal framework usable with a stent-like clot retriever device. The tapered portion of the distal body segment 128 can be shaped and otherwise configured to prevent egress of clot or clot fragments that have entered the reception space 111 between the inner and outer members 102, 103. The expanded distal struts 110 of the inner member 103 act as an additional three dimensional filter in combination with the closed end of the outer member 102 to further prevent the egress of clot or clot fragments. In certain embodiments this distal section may comprise fiber attachment points such as eyelets or other fiber attachment features and fibers may be connected to the distal section at these attachment points to create a distal net.

As illustrated in greater detail in FIGS. 2C, 3C, and 5C, the inner expandable member 103 is configured to self-expand upon release from a restraining sheath (such as a microcatheter) to a diameter D2 that is larger than the expanded diameter D1 of the outer expandable member 102 and smaller than a diameter of a blood vessel that the device 100 is configured to treat. The inner tubular member 103 includes a scaffolding that is denser, having smaller openings, compared to the outer expandable member 102. The inner tubular member 103 is configured so as to provide a flow lumen through the device 100 to facilitate the immediate restoration of blood flow past the clot upon deployment. Additionally, or alternatively, the inner tubular member 103 is configured to scaffold said flow lumen through the clot to prevent the liberation of fragments which might otherwise lodge in the distal vasculature. The inner tubular member 103 includes connected struts 131 that may contact a clot when initially deployed in a target vessel within the clot. The contact of the struts 131 of the inner tubular member 103 with the clot can provide additional grip and assists in the initial dislodgement of the clot from the vessel when the device is retracted.

Inner expandable member 103 includes a generally cylindrical section of interconnected struts 131, which is connected at its proximal end by a strut 138 (or multiple struts) to the proximal junction 112. The distal end of the inner expandable member 103 includes of an expansile section formed from expanded struts 110 which have a diameter greater than the diameter D2 of the body section of the inner tubular member 103. These expanded struts 110 are connected to a coil section 118 which in this embodiment is laser cut from the tubing that the inner expandable member 103 is also cut from during processing.

The shaft 106 can include a tapered wire shaft, and may be made of stainless steel, MP35N, Nitinol or other material of a suitably high modulus and tensile strength. Shaft 106 may have indicator bands 107 on the shaft to indicate to the user when the distal end of the device is approaching the end of the microcatheter during insertion. These bands are positioned so that as they approach a microcatheter hub or hemostasis valve they indicate the distal tip of the device is approaching the end of the microcatheter. These indicator bands can be formed by printing or removing or masking areas of shaft coating so that they are visually differentiated from the remainder of the shaft. The indicator bands 107 can additionally be recessed below the surface of the shaft 106 to give tactile feedback to the user as they approach the microcatheter.

The proximal coil 104 can extend from a distal portion of the shaft 106. The proximal coil 104 coil can be metallic and may be formed from stainless steel or from a more radiopaque material such as platinum or gold for example or an alloy of such a material. Additionally, or alternatively, the coil may be coated with a low friction material or have a polymeric jacket positioned on the outer surface of the coil. Adjacent to this coil 104 a sleeve 105 may be positioned on shaft 106. This sleeve 105 can include polymeric material and may be positioned over the tapered section of the shaft. The sleeve 105 may be rendered radiopaque through the addition of a filler material such as tungsten or barium sulphate. The sleeve 105 and shaft 106 may be coated with a material to reduce friction and thrombogenicity. The coating may consist of a polymer, a low friction lubricant such as silicon, a hydrophilic or a hydrophobic coating. This coating may also be applied to the outer member 102 and inner tubular member 103.

The outer member 102 and the inner tubular member 103 can joined at the proximal junction 112 and the distal junction 109 during assembly. To minimize tension within the members 102, 103 during use, the length of the outer member 102 can be substantially the same as the length of the inner member 103 in the freely expanded configuration and the collapsed, loaded configuration. The expanded struts 110 of the inner tubular member 103 elongate during loading so that the lengths of the inner and outer members are equal when fully loaded in a microcatheter. Length differentials between the inner member 103 and the outer member 102 can still occur when the device is deployed in a small vessel or during the loading or deployment process. The coil 118 at the distal end of the inner tubular member 103 can accommodate minor length differentials by stretching without applying significant tensile or compressive forces to the device. In another embodiment this coil 118 could be formed separately to the inner tubular member 103 and then be assembled to it. The coil 118 can be formed from a stainless steel material, a polymer or from a more radiopaque metal such as gold or platinum or an alloy of such a material. The coil 118 can also be replaced with a longitudinal length of an elastic material such as a low modulus polymer or elastomer.

In other embodiments the inner member 103 may not be connected to the distal end of the outer member 102 at all or may be constrained within the outer member 102 without being fixedly attached. In other embodiments the inner member 103 may have a non-cylindrical cross-section, may be non-uniform in diameter, and may have tailored strut patterns to provide regions of differing radial force or flexibility.

FIG. 6A shows an isometric view of another example clot retrieval device 200. Compared to the device 100 illustrated in FIGS. 1A through 5D, the outer expandable member 202 of the clot retrieval device 200 illustrated in FIG. 6A includes multiple middle body segments 227 rather than a single middle body segment 127. At least the proximal 226 and the middle body segments 227 respectively include interconnected struts, with certain struts terminating in a distal apex 233 with no distal connecting elements, and other struts terminating in junction points. The device 200 illustrated in FIG. 6A includes three middle body segments 227. According to the present invention, a clot retrieval device including features described and illustrated herein can include one, two, three, four, five, or more middle body segments. The device 200 includes an inner expandable member 203 elongated to accommodate the additional middle body segments 227 of the outer expandable member 202.

The device 200 can include a reception space 211 between the outer expandable member 202 and inner expandable member 203 configured similarly to the reception space 111 of the device 100 illustrated in FIGS. 1A through 5C.

The device 200 can further include a proximal coil 204, distal coil 208, distal junction 209, and proximal junction 212 structured similarly as corresponding components 104, 208, 209, 212 illustrated in FIGS. 1A through 5D. The device 200 can further include a sleeve, shaft, and indicator bands structured similar as corresponding components 105, 106, 107 illustrated in FIG. 1A.

FIG. 6B shows a close-up of a portion of the clot retrieval device 200 illustrated in FIG. 6A. The portion includes a tapered connecting arm 230. The connecting arm 230 can be shaped as illustrated and described in relation to tapered connecting arms 129, 130 of the device 100 illustrated in FIGS. 1A through 5C. Connecting arms 230 can join the proximal, middle, and distal body segments 226, 227, 228 and be otherwise configured in a similar manner as connecting arms 129, 130 of the device 100 illustrated in FIGS. 1A through 5C.

FIG. 7A shows a plan view of a first side of the clot retrieval device 200. FIG. 7B shows the view clot retrieval device 200 as illustrated in FIG. 7A having the inner expandable member 203 removed for the purpose of illustration. FIG. 7C shows the view of the clot retrieval device 200 as illustrated in FIG. 7A having the outer expandable member 202 removed for the purpose of illustration.

The outer expandable member 202 of the device 200 can include a proximal struts 220 and a proximal body segment 226 structured similarly to the proximal struts 120 and proximal body segment 126 of the device 100 illustrated in FIGS. 1A through 5C. The outer expandable member 202 can include a distal body segment 228 structured similarly to the distal body segment 128 of the device 100 illustrated in FIGS. 1A through 5C. The outer expandable member 202 can include radiopaque markers 216, 221, 225 positioned and otherwise configured similarly to corresponding markers 116, 121, 125 of the device 100 illustrated in FIGS. 1A through 5C. The outer expandable member 202 can include inlet mouths 222 configured similarly to inlet mouths 122 of the device 100 illustrated in FIGS. 1A through 5C.

The inner expandable member 203 can include distal crown struts 210, interconnecting struts 231 in a tubular body portion, and proximal connecting struts 234 similar to corresponding struts 110, 131, 138 of the device 100 illustrated in FIGS. 1A through 5C. The inner expandable member 203 can be connected to an inner coil 218 configured similar to the inner coil 118 of the device 100 illustrated in FIGS. 1A through 5C.

FIG. 8A shows a plan view of a second side of the clot retrieval device illustrated in FIG. 6A, the second side viewed at 90° from the first side view illustrated in FIG. 7A. FIG. 8B shows the view clot retrieval device 200 as illustrated in FIG. 8A having the inner expandable member 203 removed for the purpose of illustration. FIG. 8C shows the view of the clot retrieval device 200 as illustrated in FIG. 8A having the outer expandable member 202 removed for the purpose of illustration.

FIG. 9 shows a linear view of the outer expandable member 202 cut along a centerline B-B indicated in FIGS. 7B and 8B and flattened. A portion of the outer expandable member 202 as indicated in FIG. 9 can be configured as illustrated in FIG. 4B and further as illustrated in FIG. 4C. For instance, radiopaque markers 221 can be staggered as illustrated in greater detail in FIG. 4B. Connecting arms 230 can be tapered and otherwise configured as arms 129 illustrated in greater detail in FIGS. 4B and 4C. Struts and joints of the outer expandable member 202 can be shaped and otherwise configured to correspond to joints and struts 144, 145, 146, 147, 150, 151 illustrated in FIGS. 4B and 4C.

FIG. 10A shows a plan view of a distal end of the clot retrieval device 200. FIG. 10B shows the view clot retrieval device 200 as illustrated in FIG. 10A having the inner expandable member 203 removed for the purpose of illustration. FIG. 10C shows the view of the clot retrieval device 200 as illustrated in FIG. 10A having the outer expandable member 202 removed for the purpose of illustration.

Figure 11A:
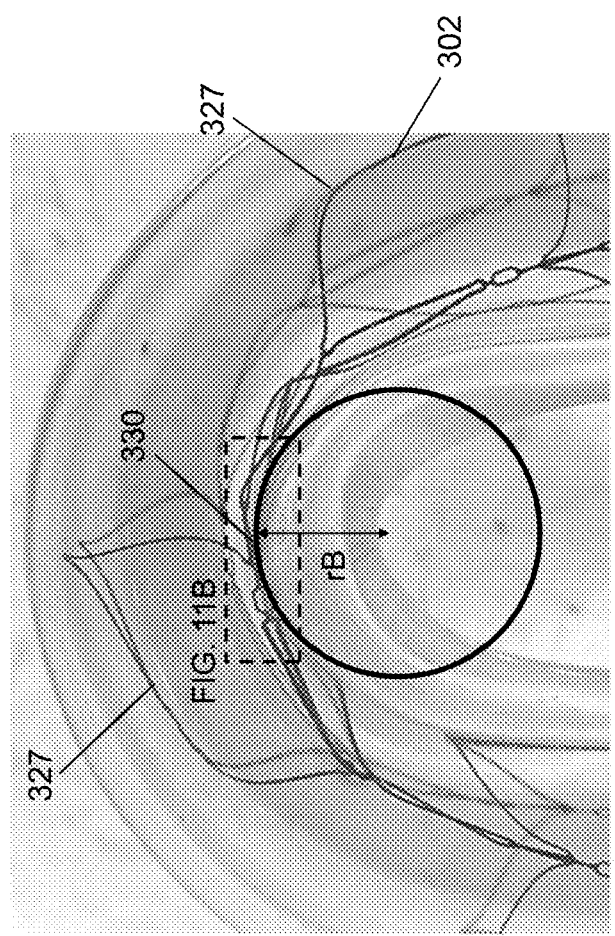
FIG. 11A shows an example outer expandable member traversing a lumen having a 360° bend according to aspects of the present invention.

FIG. 11A shows an example outer expandable member 302 traversing a lumen having a 360° bend with a radius of curvature rB at the apex of the bend. Because the outer expandable member 302 closely follows the bend of lumen, the outer expandable member has a radius of curvature that is approximately equal to the radius of curvature rB of the lumen. FIG. 11B shows a close-up of a portion of the outer expandable member 302 as indicated in FIG. 11A. The outer expandable member 302 includes tapered connecting arms 330 between body segments 327 configured similarly to the connecting arms 129, 130, 230 of the devices 100, 200 illustrated in FIGS. 1A through 10C. As shown in greater detail in FIG. 11B, the outer expandable member 302 has a curvature with a radius rA at a narrow area of the connecting arm 330 that is smaller than the overall radius of curvature rB of the outer expandable member 302 around the bend the lumen. In other words, the connecting arm 330 provides a bending point for the outer expandable member 302. The flexibility of the connecting arm 330 can allow the body segments 327 to extend juxtaposed to a lumen (e.g. the illustrated lumen and/or a blood vessel lumen) to a greater extent than a similarly structured outer expandable member having less flexible connecting arms. In one example, the outer expandable member 302 can be configured to bend with a curvature having a radius rA at the narrow area of the connecting arm 330 of approximately 0.5 millimeters (mm) or greater including 0.6 mm, 0.7 mm, 0.8 mm, 0.9 mm, and 1.0 mm.

Figure 12A:
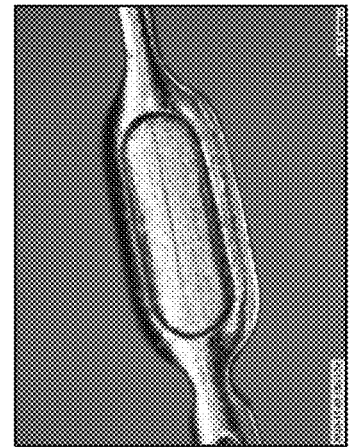
FIG. 12A shows an illustration of a portion of an example expandable member having a radiopaque marker according to aspects of the present invention.
Figure 12B:
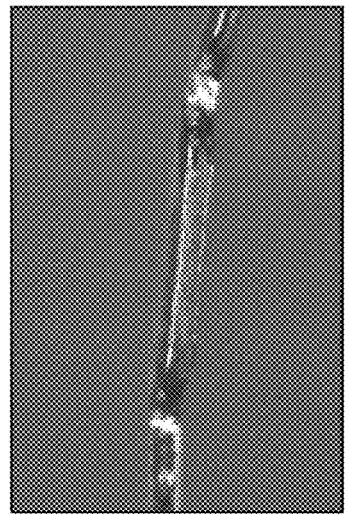
FIG. 12B shows a side view of the portion of the expandable member illustrated in FIG. 12A.

FIG. 12A shows an illustration of a portion of an example expandable member having a radiopaque marker. FIG. 12B shows a side view of the portion of the expandable member illustrated in FIG. 12A. Some or all of the markers 116, 121, 125, 216, 221, 225 of the devices illustrated and described herein can be shaped similar to the marker illustrated in FIGS. 12A and 12B.

Figure 13B:
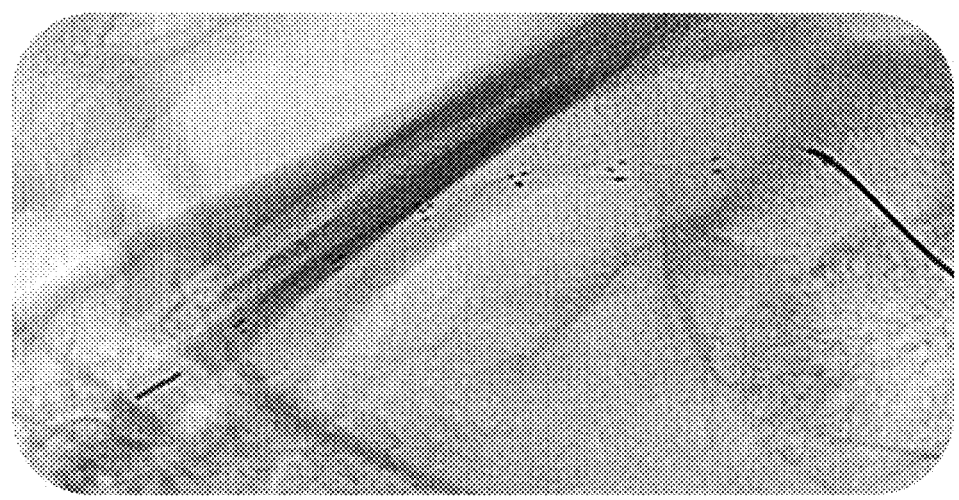
FIGS. 13A and 13B are radiographic images of an example clot retrieval device according to aspects of the present invention.
Figure 13A:
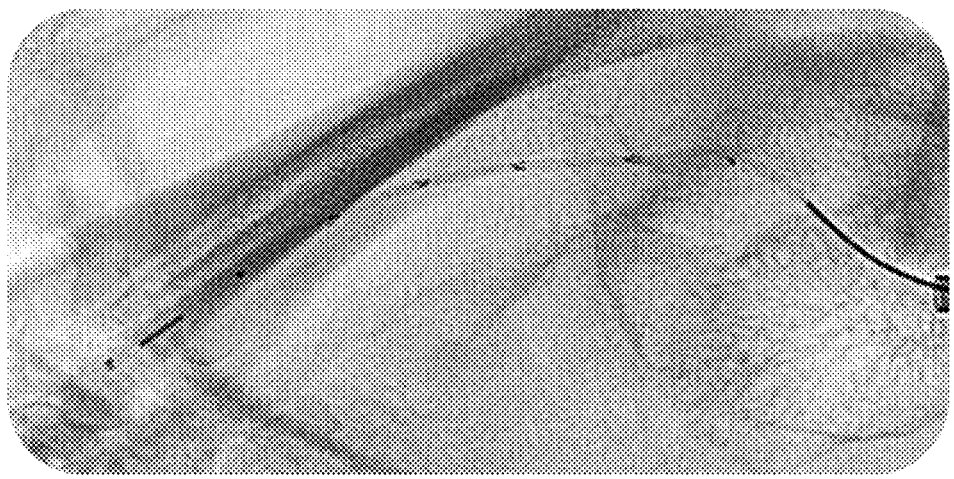

FIGS. 13A and 13B are radiographic images of an example clot retrieval device according to aspects of the present invention. Radiopaque material in the distal coil, proximal coil, and markers appear dark in the radiographic images.

A clot retrieval device according to the teachings herein can be sized to accommodate a variety of treatment needs. Dimension such as overall length L1 of the outer expandable member, working length L2 of the device, diameter D1 of the outer expandable member D1, and diameter D2 of the inner expandable member can be measured as indicated in FIGS. 2A through 2C and 7A through 7C.

In one example device, when freely expanded, the outer expandable member can have an overall length L1 about 34 mm, a working length L2 of about 22 mm, and a diameter D1 of about 5 mm. The inner expandable member tubular body diameter D2 can measure less than the outer expandable member diameter, preferably about 1 mm and more preferably about 1.22 mm. Configured as such, the example device can be suitable for treating blood vessels having a diameter between about 1.5 mm and about 5 mm. The outer expandable member of the example device preferably includes a proximal body segment, exactly one middle body segment, and a distal body segment similar to the proximal body segment 126, middle body segment 127, and distal body segment 128 of the device 100 illustrated in FIGS. 1A through 5C.

In another example device, when freely expanded, the outer expandable member can have an overall length L1 about 49 mm, a working length L2 of about 37 mm, and a diameter D1 of about 5 mm. The inner expandable member tubular body diameter D2 can measure less than the outer expandable member diameter, preferably about 1 mm and more preferably about 1.22 mm. Configured as such, the example device can be suitable for treating blood vessels having a diameter between about 1.5 mm and about 5 mm. The outer expandable member of the example device preferably includes a proximal body segment, exactly three middle body segment, and a distal body segment similar to the proximal body segment 226, middle body segments 227, and distal body segment 228 of the device 200 illustrated in FIGS. 6A through 10C.

In another example device, when freely expanded, the outer expandable member can have an overall length L1 about 57 mm, a working length L2 of about 45 mm, and a diameter D1 of about 6.5 mm. The inner expandable member tubular body diameter D2 can measure less than the outer expandable member diameter, preferably about 1 mm and more preferably about 1.22 mm. Configured as such, the example device can be suitable for treating blood vessels having a diameter between about 1.5 mm and about 6.5 mm. The outer expandable member of the example device preferably includes a proximal body segment, exactly three middle body segment, and a distal body segment similar to the proximal body segment 226, middle body segments 227, and distal body segment 228 of the device 200 illustrated in FIGS. 6A through 10C.

In some examples, a clot retrieval device according to the teachings herein can be dimensioned such that markers on body segments (e.g. markers 121, 221 on body segments 126, 127, 128, 226, 227, 228 illustrated herein) illustrated herein can be separated in the longitudinal direction (in the direction of the longitudinal axis A-A) from one or more markers on an adjacent body segment by about 10 mm when the clot retrieval device is collapsed for delivery across a clot and can be separated by about 8 mm in the longitudinal direction when the clot retrieval device is freely expanded.

Figure 14:
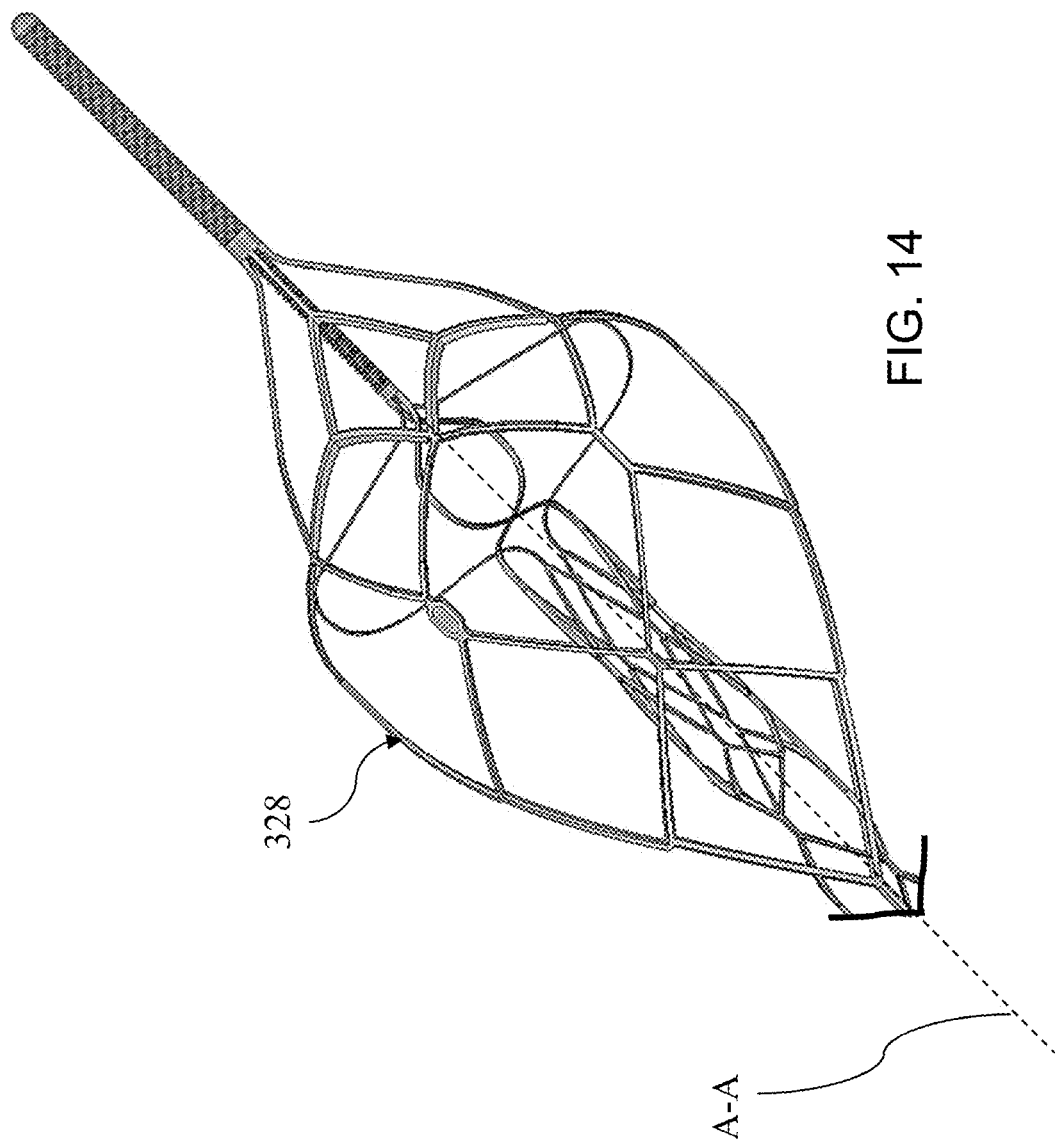
FIG. 14 shows an illustration of an alternative distal portion of an example clot retrieval device according to aspects of the present invention.

FIG. 14 illustrates an alternative distal portion of an example clot retrieval device described in greater detail in a U.S. Non-Provisional Patent Application titled "A CLOT RETRIEVAL DEVICE FOR REMOVING CLOT FROM A BLOOD VESSEL" filed concurrently herewith and incorporated by reference as if set forth in its entirety herein.

In some examples, a clot retrieval device according to the teachings herein can have alternative geometries suitable for clot retrieval devices. For instance, the clot retrieval device can include a distal portion configured as illustrated in FIG. 14. The outer expandable member can include a distal body portion configured similar to the distal body portion 328 illustrated in FIG. 14. Alternatively, the distal portion of the clot retrieval device need not be configured to capture clot fragments and can for instance can have large cell openings or be completely open. Further, in some examples, the clot retrieval device need not include an inner body.

As discussed herein, a "patient" or "subject" can be a human or any animal. It should be appreciated that an animal can be a variety of any applicable type, including, but not limited to, mammal, veterinarian animal, livestock animal or pet-type animal, etc. As an example, the animal can be a laboratory animal specifically selected to have certain characteristics similar to a human (e.g., rat, dog, pig, monkey, or the like).

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±20% of the recited value, e.g. "about 90%" may refer to the range of values from 71% to 99%. Ranges can be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It must also be noted that, as used in the specification and the appended claims, the singular forms "a," "an," and "the" include plural referents unless the context clearly dictates otherwise.

In describing examples, terminology is resorted to for the sake of clarity. It is intended that each term contemplates its broadest meaning as understood by those skilled in the pertinent art and includes all technical equivalents that operate in a similar manner to accomplish a similar purpose. It is also to be understood that the mention of one or more steps of a method does not preclude the presence of additional method steps or intervening method steps between those steps expressly identified. Steps of a method can be performed in a different order than those described herein without departing from the scope of the disclosed technology. Similarly, it is also to be understood that the mention of one or more components in a device or system does not preclude the presence of additional components or intervening components between those components expressly identified.

The descriptions contained herein are examples of the disclosure and are not intended in any way to limit the scope of the disclosure. While particular examples of the present disclosure are described, various modifications to devices and methods can be made without departing from the scope and spirit of the disclosure. For example, while the examples described herein refer to particular components, the disclosure includes other examples utilizing various combinations of components to achieve a described functionality, utilizing alternative materials to achieve a described functionality, combining components from the various examples, combining components from the various example with known components, etc. The disclosure contemplates substitutions of component parts illustrated herein with other well-known and commercially-available products. The scope of the claims which follow are intended to include such modifications as apparent to those having skill in the pertinent art as understood according to the teachings herein.

What is claimed is:

1. A clot retrieval device comprising a collapsed configuration and an expanded configuration and being configured to remove a clot from a blood vessel, the device comprising:
    an inner expandable member comprising a first framework of struts that form closed cells; and
    an outer expandable member comprising a second framework of struts that form closed cells larger than the closed cells of the inner expandable member and that at least partially radially surround the inner expandable member,
        the outer expandable member comprising a first body segment and a second body segment connected by two connecting arms,
        the first body segment being positioned in a proximal direction in relation the second body segment, and
        each of the two connecting arms respectively comprising a tapered shape being wider approximate the first body segment and narrower approximate the second body segment: and
    wherein at least one of the first body segment and the second body segment comprises four or more radiopaque markers positioned around a circumference of the respective body segment, wherein, when the clot retrieval device is in the collapsed configuration, each of the radiopaque markers is offset and staggered along a longitudinal axis of the device to facilitate collapse of a circumference of the outer expandable member.

2. The clot retrieval device of claim 1, wherein the outer expandable member comprises two inlet mouths in the second framework, each of the two inlet mouths comprising a respective opening bounded by the first body segment, the second body segment, and the two connecting arms.

3. The clot retrieval device of claim 2, wherein the first body segment comprises two pairs of struts each terminating in a respective distal apex and forming a proximal boundary of a respective inlet mouth of the two inlet mouths.

4. The clot retrieval device of claim 1, wherein the two connecting arms extend substantially parallel to a longitudinal axis of the device.

5. The clot retrieval device of claim 1, wherein the two connecting arms are positioned approximately 180° from each other about a circumference of the outer expandable member.

6. The clot retrieval device of claim 1, wherein the first body segment and the second body segment are connected to each other solely via the two connecting arms.

7. The clot retrieval device of claim 1, wherein each of the two connecting arms is configured to bend with a curvature having a radius smaller than a radius of curvature of a majority of struts of the first body segment and the second body segment as the clot retrieval device is pulled proximally through a tubular vasculature comprising a bend of about 180°.

8. The clot retrieval device of claim 1,
    wherein the outer expandable member further comprises three or more body segments in addition to the first body segment and the second body segment, each of the three or more body segments shaped substantially similarly to the first body segment and the second body segment, and
    wherein the outer expandable member comprises pairs of tapered connecting arms such that each respective pair of tapered connecting arms joins longitudinally adjacent body segments of the three or more body segments.

9. The clot retrieval device of claim 1, wherein when the clot retrieval device is in the collapsed configuration, alternating radiopaque markers of the four or more radiopaque markers are aligned in a plane orthogonal to the longitudinal axis.

10. The clot retrieval device of claim 1,
wherein the first body segment comprises a first set of four or more radiopaque markers,
wherein the second body segment comprises a second set of four or more radiopaque markers,
wherein, when the clot retrieval device is in the expanded configuration, the first and second sets of four or more radiopaque markers are spaced approximately 8 millimeters apart measured in the direction of the longitudinal axis, and
wherein, when the clot retrieval device is in the collapsed configuration, the first and second sets of four or more radiopaque markers are spaced approximately 10 millimeters apart measured in the direction of the longitudinal axis.

11. The clot retrieval device of claim 1, wherein each of the four or more radiopaque markers comprises radiopaque material positioned in an eyelet.

12. The clot retrieval device of claim 1, wherein at least two of the four or more radiopaque markers are aligned, in the direction of the longitudinal axis, with a respective connecting arm of the two connecting arms.

13. A clot retrieval device comprising a collapsed configuration and an expanded configuration and configured to remove a clot from a blood vessel, the device comprising:
an inner expandable member comprising a first framework of struts that form closed cells; and
an outer expandable member comprising:
a second framework of struts that form closed cells larger than the closed cells of the inner expandable member and that at least partially radially surround the inner expandable member, and
four or more radiopaque markers affixed to the second framework of struts and positioned to indicate a circumference of the outer expandable member and further positioned such that when the clot retrieval device is in the collapsed configuration, each of the radiopaque markers is offset and staggered along a longitudinal axis of the device to facilitate collapse of a circumference of the outer expandable member.

14. The clot retrieval device of claim 13,
wherein the outer expandable member comprises discontinuous body segments spaced apart from each other in the direction of the longitudinal axis, and
wherein the four or more radiopaque markers are positioned to indicate a circumference of a body segment of the discontinuous body segments.

15. The clot retrieval device of claim 14,
wherein the body segments comprise a first body segment and a second body segment, the first body segment being positioned in a proximal direction in relation to the second body segment,
wherein the outer expandable member comprises two connecting arms joining the first body segment to the second body segment, and
wherein each of the two connecting arms respectively comprises a tapered shape being wider approximate the first body segment and narrower approximate the second body segment.

16. The clot retrieval device of claim 15, wherein at least two of the four or more radiopaque markers are aligned, in the direction of the longitudinal axis, with a respective connecting arm of the two connecting arms.

17. The clot retrieval device of claim 15, wherein the outer expandable member comprises two inlet mouths in the second framework, each of the two inlet mouths comprising a respective opening bounded by the first body segment, the second body segment, and the two connecting arms.

18. The clot retrieval device of claim 15,
wherein the first body segment comprises the four or more radiopaque markers forming a first set of markers, and
wherein the second body segment comprises a second set of four or more radiopaque markers positioned to indicate a circumference of the second body segment and further positioned such that when the clot retrieval device is in the collapsed configuration, each of the radiopaque markers of the second set is offset, in relation to a longitudinal axis of the device to respective adjacent radiopaque markers of the second set.

19. The clot retrieval device of claim 15,
wherein the two connecting arms are positioned approximately 180° from each other about a circumference of the outer expandable member.

* * * * *